United States Patent
Majeed et al.

(10) Patent No.: US 12,053,500 B2
(45) Date of Patent: Aug. 6, 2024

(54) COMPOSITIONS FOR MANAGEMENT OF ACUTE NEPHROTOXICITY

(71) Applicant: Sami-Sabinsa Group Limited, Bangalore (IN)

(72) Inventors: Muhammed Majeed, Bangalore (IN); Kalyanam Nagabhushanam, East Windsor, NJ (US); Lakshmi Mundkur, Bangalore (IN); A. Muhamad Ibrahim, Bangalore (IN)

(73) Assignee: SAMI-SABINSA GROUP LIMITED, Bangalore (IN)

( * ) Notice: Subject to any disclaimer, the term of this patent is extended or adjusted under 35 U.S.C. 154(b) by 0 days.

(21) Appl. No.: 17/644,990

(22) Filed: Dec. 17, 2021

(65) Prior Publication Data

US 2022/0193178 A1  Jun. 23, 2022

Related U.S. Application Data

(60) Provisional application No. 63/126,920, filed on Dec. 17, 2020.

(51) Int. Cl.
| | |
|---|---|
| A61K 36/9066 | (2006.01) |
| A23L 33/105 | (2016.01) |
| A61K 9/00 | (2006.01) |
| A61K 9/20 | (2006.01) |
| A61K 9/48 | (2006.01) |
| A61K 31/12 | (2006.01) |
| A61K 31/19 | (2006.01) |
| A61K 31/23 | (2006.01) |
| A61K 36/324 | (2006.01) |
| A61K 47/12 | (2006.01) |
| A61K 47/26 | (2006.01) |
| A61K 47/42 | (2017.01) |
| A61P 3/06 | (2006.01) |
| A61P 19/02 | (2006.01) |
| A61P 39/06 | (2006.01) |

(52) U.S. Cl.
CPC ........ *A61K 36/9066* (2013.01); *A23L 33/105* (2016.08); *A61K 9/0053* (2013.01); *A61K 9/0056* (2013.01); *A61K 9/2009* (2013.01); *A61K 9/2013* (2013.01); *A61K 9/2054* (2013.01); *A61K 9/2059* (2013.01); *A61K 9/4866* (2013.01); *A61K 31/12* (2013.01); *A61K 31/19* (2013.01); *A61K 31/23* (2013.01); *A61K 36/324* (2013.01); *A61K 47/12* (2013.01); *A61K 47/26* (2013.01); *A61K 47/42* (2013.01); *A61P 3/06* (2018.01); *A61P 19/02* (2018.01); *A61P 39/06* (2018.01)

(58) Field of Classification Search
None
See application file for complete search history.

(56) References Cited

U.S. PATENT DOCUMENTS

| | | | |
|---|---|---|---|
| 2014/0193533 A1* | 7/2014 | Antony | A61K 31/12 424/756 |
| 2019/0192447 A1* | 6/2019 | Majeed | A61K 36/71 |

OTHER PUBLICATIONS

Assi (Comparative Clinical Pathology (2018), vol. 27, pp. 705-716).*
Kabeer (Biomedical Research and Therapy (Mar. 2019), vol. 6, No. 3, pp. 3053-3066).*

* cited by examiner

*Primary Examiner* — Susan Hoffman
(74) *Attorney, Agent, or Firm* — Arentfox Schiff LLP

(57) ABSTRACT

A composition enriched with bisdemethoxycurcumin standardized to contain 20-80% w/w bisdemethoxycurcumin, 10-35% w/w demethoxycurcumin and 10-50% w/w curcumin. More specifically the invention discloses the potential of a composition comprising 20-80% w/w bisdemethoxycurcumin, 10-35% w/w demethoxycurcumin and 10-50% w/w curcumin in the management of nephrotoxicity in mammals. The composition further comprises a *Nigella sativa* extract standardised to contain not less than 2% w/w thymoquinone and about 0.01%-10% w/w thymohydroquinone.

27 Claims, 16 Drawing Sheets

Specification includes a Sequence Listing.

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcaggatgcg tccaccaaga ag                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgtgtccacg gcggcaatca tc                                              22

<210> SEQ ID NO 3
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gagtacctga accggcatct                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gaaatcaaac agaggtcgca                                                    20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gagaagcagc ttcctgttct gg                                                 22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtgtccgttc accaacagga ag                                                 22

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cccgcgagta caaccttct                                                     19

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cgtcatccat ggcgaact                                                      18

<210> SEQ ID NO 9
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
actgaacttc ggggtgattg                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcttggtggt ttgctacgac                                                  20

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agtctgaaga actattttaa ctcaagtagc at                                    32

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ctggctctca agtattttcg tgttac                                           26
```

COMPOSITIONS FOR MANAGEMENT OF ACUTE NEPHROTOXICITY

CROSS REFERENCE TO RELATED APPLICATIONS

This is a non-provisional US patent application claiming priority from U.S. Provisional application 63/126,920, filed on 17 Dec. 2020, the details of which are being incorporated herein by reference.

SEQUENCE LISTING

The instant application contains a Sequence Listing which has been submitted electronically in ASCII format and is hereby incorporated by reference in its entirety. Said ASCII copy, created on Apr. 19, 2024, is named 108064_09023_SL.txt and is 3,095 bytes in size.

BACKGROUND OF THE INVENTION

Field of Invention

The present invention relates to nephroprotective compositions and methods for managing acute nephrotoxicity. More specifically the invention relates to the potential of a curcuminoid 10-35% w/w composition comprising 20-80% w/w bisdemethoxycurcumin, demethoxycurcumin and 10-50% w/w curcumin for the therapeutic management of acute nephrotoxicity. The composition further comprises *Nigella sativa* extract standardised to contain thymoquinone and thymohydroquinone.

Description of Prior Art

Nephrotoxicity or renal toxicity is defined as a condition in which rapid deterioration in kidney function occurs due to toxic nature of drugs and other chemicals. Different mechanisms lead to nephrotoxicity, including renal tubular toxicity, inflammation, glomerular damage, crystal nephropathy, and thrombotic microangiopathy (Al-Naimi et al., Nephrotoxicity: Role and significance of renal biomarkers in the early detection of acute renal injury, J Adv Pharm Technol Res. 2019 July-September; 10(3): 95-99). There are different agents that are nephrotoxic and cause acute renal injury which include drugs, ethylene glycol, carbon tetrachloride, sodium oxalate and heavy metals such as lead, mercury, cadmium and arsenic biological agents such as viruses, mould and fungi, interferons, recombinant leukocytes, antibiotics etc (Santos et al., Nephrotoxicity in cancer treatment: An overview World J Clin Oncol. 2020 Apr. 24; 11(4): 190-204). These agents adversely affect the kidney resulting in acute renal failure, chronic interstitial nephritis and nephritic syndrome. Although the condition is asymptomatic and are diagnosed by observed elevations in blood urea nitrogen (BUN) and serum creatinine levels, common symptoms include anorexia, fatigue, mental status changes, nausea, vomiting, and pruritus (Howell et al., Drug-Induced Acute Renal Failure, US Pharm. 2007; 32(3):45-50).

The following drugs are reported to have a toxic effect on the kidneys:

Antineoplastic agents: Alkylating agents: Cisplatin, cyclophosphamide; Nitrosoureas: Streptozotocin; Antimetabolites: Methotrexate, Cytosine Antitumor antibiotics: Mitomycin, Doxorubicin; Biologic agents: Recombinant leukocyte and interferon Antimicrobial agents: Tetracycline, Sulphadiazine, Trimethoprin, Rifampicin, Amphotericin B Gentamycin, Amikacin, Kanamycin, Streptomycin Antivirals: Acyclovir, Indinavir, Foscarnet, Tenofovir In addition to the above, viruses and drugs used for the treatment of viral diseases have a toxic effect of the kidney. Sars-COV-2, the virus responsible for the COVID 19 pandemic is also reported to cause nephrotoxicity (Qian J, -Y, Wang B, Liu B, -C: Acute Kidney Injury in the 2019 Novel Coronavirus Disease. Kidney Dis 2020; 6:318-323). Further, the drugs which were administered for treating COVID 19 symptoms can increase the toxic load on the kidneys thereby accelerating damage and causing renal failure.

The current treatment modalities include identification of the cause of kidney injury and treating life threatening features and attempting to halt or reverse the decline in renal function. Providing renal replacement therapy can also be considered in severe conditions. The following reference disclose the treatments employed for the management of acute real injury and nephrotoxicity:

a. Fry et al., Management of acute renal failure, Postgrad Med J. 2006; 82(964): 106-116.
b. Chapman et al., Reversibility of cyclosporin nephrotoxicity after three months' treatment, The Lancet, 1985; 325 (8421): 128-130.
c. Ali et al., The Effect of Treatment with Gum Arabic on Gentamicin Nephrotoxicity in Rats: A Preliminary Study, Renal Failure, 2003; 25:1, 15-20, DOI: 10.1081/JDI-120017439.
d. Fouad et al., Coenzyme Q10 treatment ameliorates acute cisplatin nephrotoxicity in mice, Toxicology, 2010; 274 (1-3): 49-56.

Natural molecules from medicinal plants are very effective in managing and reducing the symptoms of acute real injury and nephrotoxicity. It is well known in the scientific art regarding the compounds obtained from *Curcuma* species, specifically curcuminoids, and their role in therapeutic management of various diseases and disorders are well documented. The metabolites of curcumin—demethoxycurcumin, bisdemethoxycurcumin, tetrahydrocurcuminoids, hexahydrocurcuminoids, and octahydrocurcuminoids are garnering much attention owing to their similar and superior efficacy over curcumin (Majeed et al., Reductive Metabolites of Curcuminoids, Nutriscience Publishers LLC, 2019).

Bisdemethoxycurcumin is reported to have superior effect over curcumin in managing certain pathological conditions (Franco Caveleri, U.S. Ser. No. 10/945,970) and is also reported to nullify the effects of drug induced nephrotoxicity (Jin et al., Bisdemethoxycurcumin attenuates cisplatin-induced renal injury through anti-apoptosis, anti-oxidant and anti-inflammatory, Eur J Pharmacol, 2020; 874:173026. doi: 10.1016/j.ejphar.2020.173026. Epub 2020 Feb 20). Other natural extracts are also effective in reducing the symptoms of nephrotoxicity (Alsuhaibani et al., Effect of *Nigella sativa* against cisplatin induced nephrotoxicity in rats, Ital J Food Saf. 2018; 7(2): 7242).

Since nephrotoxicity causes renal tubular toxicity, inflammation, glomerular damage, crystal nephropathy, and thrombotic microangiopathy and is a multi-factorial disorder, a single drug which treats only one of the above conditions may not be a viable option to improve the symptoms. There still exists an unmet industrial need to find a synergistic composition that is effective in managing all the symptoms of acute real injury. The present invention solves this unmet need by disclosing a composition comprising 20-80% w/w bisdemethoxycurcumin, 10-35% w/w demethoxycurcumin and 10-50% w/w curcumin. This composition along with Nigella sativa extract standardised to contain not less than 2% w/w thymoquinone, about 0.01%-10% w/w thymohydroquinone, about 15%-95% w/w fatty acids, about 0.001%-3% w/w hederagenin or hederin is useful in addressing all the causative factors that lead to the development of nephrotoxicity and is a complete nephroprotective agent.

It is the principal object of the invention to disclose a composition comprising 20-80% w/w bisdemethoxycurcumin, 10-35% w/w demethoxycurcumin and 10-50% w/w curcumin.

It is another object of the invention to disclose a method for managing acute renal toxicity in mammals using a composition comprising 20-80% w/w bisdemethoxycurcumin, 10-35% w/w demethoxycurcumin and 10-50% w/w curcumin. The composition further comprises Nigella sativa extract standardised to contain not less than 2% w/w thymoquinone, about 0.01%-10% w/w thymohydroquinone, about 15%-95% w/w fatty acids, about 0.001%-3% w/w hederagenin or hederin.

The present invention fulfils the abovementioned objects and provides further related advantages.

SUMMARY OF THE INVENTION

In a most preferred embodiment, the invention discloses a composition comprising 20-80% w/w bisdemethoxycurcumin, 10-35% w/w demethoxycurcumin and 10-50% w/w curcumin.

In another preferred embodiment, the invention discloses a curcuminoid composition comprising 20-80% w/w bisdemethoxycurcumin, 10-35% w/w demethoxycurcumin and 10-50% w/w curcumin and Nigella sativa extract standardised to contain not less than 2% w/w thymoquinone, about 0.01%-10% w/w thymohydroquinone, about 15%-95% w/w fatty acids, about 0.001%-3% w/w hederagenin or hederin.

In another most preferred embodiment, the invention discloses a method for the management of toxicity in mammalian kidney cells, said method comprising step of bringing into contact mammalian kidney cells with a composition comprising 20-80% w/w bisdemethoxycurcumin, 10-35% w/w demethoxycurcumin and 10-50% w/w curcumin, to reduce to toxic effects in the cells.

In another most preferred embodiment, the invention discloses a method for the management of toxicity in mammalian kidney cells, said method comprising step of bringing into contact mammalian kidney cells with a curcuminoid composition comprising 20-80% w/w bisdemethoxycurcumin, 10-35% w/w demethoxycurcumin and 10-50% w/w curcumin and Nigella sativa extract standardised to contain not less than 2% w/w thymoquinone, about 0.01%-10% w/w thymohydroquinone, about 15%-95% w/w fatty acids, about 0.001%-3% w/w hederagenin or hederin, to reduce to toxic effects in the cells.

In another most preferred embodiment, the invention discloses a curcuminoid composition comprising 20-80% w/w bisdemethoxycurcumin, 10-35% w/w demethoxycurcumin and 10-50% w/w curcumin, for the management of toxicity in mammalian kidney cells.

In another most preferred embodiment, the invention discloses a curcuminoid composition comprising 20-80% w/w bisdemethoxycurcumin, 10-35% w/w demethoxycurcumin and 10-50% w/w curcumin and Nigella sativa extract standardised to contain not less than 2% w/w thymoquinone, about 0.01%-10% w/w thymohydroquinone, about 15%-95% w/w fatty acids, about 0.001%-3% w/w hederagenin or hederin, for the management of toxicity in mammalian kidney cells.

In another most preferred embodiment, the invention discloses a method for the therapeutic management of nephrotoxicity in mammals, said method comprising step of administering an effective dose of a composition comprising 20-80% w/w bisdemethoxycurcumin, 10-35% w/w demethoxycurcumin and 10-50% w/w curcumin, to mammals with symptoms of nephrotoxicity to bring about nephroprotection.

In another most preferred embodiment, the invention discloses a method for the therapeutic management of nephrotoxicity in mammals, said method comprising step of administering an effective dose of a composition comprising 20-80% w/w bisdemethoxycurcumin, 10-35% w/w demethoxycurcumin and 10-50% w/w curcumin and Nigella sativa extract standardised to contain not less than 2% w/w thymoquinone, about 0.01%-10% w/w thymohydroquinone, about 15%-95% w/w fatty acids, about 0.001%-3% w/w hederagenin or hederin, to mammals with symptoms of nephrotoxicity to bring about nephroprotection.

In another most preferred embodiment, the invention discloses a composition comprising 20-80% w/w bisdemethoxycurcumin, 10-35% w/w demethoxycurcumin and 10-50% w/w curcumin for the therapeutic management of nephrotoxicity in mammals.

In another most preferred embodiment, the invention discloses a composition comprising 20-80% w/w bisdemethoxycurcumin, 10-35% w/w demethoxycurcumin and 10-50% w/w curcumin and Nigella sativa extract standardised to contain not less than 2% w/w thymoquinone, about 0.01%-10% w/w thymohydroquinone, about 15%-95% w/w fatty acids, about 0.001%-3% w/w hederagenin or hederin for the therapeutic management of nephrotoxicity in mammals.

Other features and advantages of the present invention will become apparent from the following more detailed description, which illustrate, by way of example, the principle of the invention.

DETAILED DESCRIPTION OF PREFERRED EMBODIMENTS

Figure 1:
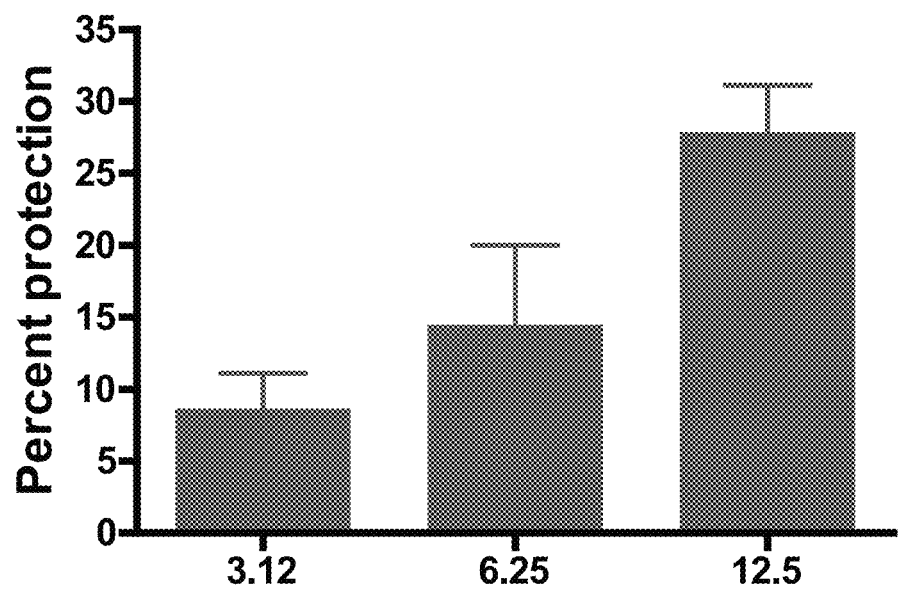
FIG. 1 is a graphical representation showing the nephroprotective effects (MTT assay) of a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin.

In a most preferred embodiment, the invention discloses a composition comprising 20-80% w/w bisdemethoxycurcumin, 10-35% w/w demethoxycurcumin and 10-50% w/w curcumin. In a further related aspect, the composition comprises of 30-70% bisdemethoxycurcumin, 10-25% w/w demethoxycurcumin and 30-50% w/w curcumin. In a further aspect, the composition comprises 40-60% bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 30-50% w/w curcumin. In yet another related aspect, the total curcuminoids in the composition are in the range of 20-95% w/w. In a further aspect, the composition is isolated and formulated using a process comprising steps of:

a. Extracting the turmeric raw material using organic solvent in a quantity of 3-5 times the volumes of raw material, under a controlled temperature of 50-70° C. with constant stirring for 2-3 hours to yield a filtrate, b. Repeating the process of step a) to yield a filtrate and marc of turmeric, c. Extracting the marc of step b) with organic solvent in a quantity of 3-5 times the volumes of marc at a temperature of 55-80° C., to obtain a filtrate d. Repeating the process of step c) 3-4 times and pooled the filtrate to obtain a turmeric oleoresin with 10-25% w/w BDMC, 8-20% w/w DMC and Curcumin 10-25% w/w, wherein the total Curcuminoids content is 30-60% w/w by HPLC.

e. Crystallizing the olcoresin of step d) with a mixture organic solvents at 0-5° C. for 3-4 hours,
f. Filtering under vacuum at a temperature of 20-30° C., to obtain a residue and a filtrate,
g. Drying the residue of step f), to obtain a dry powder
h. Reducing the volume of filtrate of step f) to half and recrystallizing using organic solvent at 20-30° C. overnight,
i. Filtering and drying the crystals to obtain a crystalline powder
j. Blended the fractions of step g) and i) to obtain a composition comprising Curcumin—24-45%; demethoxycurcumin—10-25% and bisdemethoxycurcumin—20-50% w/w.

In a related aspect, the solvent of step a) can be selected from the group consisting of hexane, heptane, petroleum ether and the solvent of step c), e) and h) can be selected from the group consisting of acetic acid, acetone, ethanol, ethyl acetate, hexane, heptane, isopropanol, methanol, n-Propanol, pentane, toluene, water or combinations thereof. In a further related aspect, the composition further comprises of stabilizing agents, bioavailability enhancers and antioxidants, pharmaceutically or nutraceutically or cosmeceutically accepted excipients and enhancers and administered orally in the form of tablets, capsules, syrups, gummies, powders, suspensions, emulsions, chewables, candies or eatables.

In another preferred embodiment, the invention discloses a curcuminoid composition comprising 20-80% w/w bisdemethoxycurcumin, 10-35% w/w demethoxycurcumin and 10-50% w/w curcumin and *Nigella sativa* extract standardised to contain not less than 2% w/w thymoquinone, about 0.01%-10% w/w thymohydroquinone, about 15%-95% w/w fatty acids, about 0.001%-3% w/w hederagenin or hederin. In a further related aspect, the curcuminoid composition comprises of 30-70% bisdemethoxycurcumin, 10-25% w/w demethoxycurcumin and 30-50% w/w curcumin. In a further aspect, the curcuminoid composition comprises 40-60% bisdemethoxycurcumin, 10-25% w/w demethoxycurcumin and 30-50% w/w curcumin. In another related aspect, the curcuminoid composition comprises of 30-50% w/w bisdemethoxycurcumin, 10-25% w/w demethoxycurcumin and 30-50% w/w curcumin. In another related aspect, the curcuminoid composition comprises of 30-50% w/w bisdemethoxycurcumin, 10-25% w/w demethoxycurcumin and 25-45% w/w curcumin. In another related aspect, the curcuminoid composition comprises of 20-50% w/w bisdemethoxycurcumin, 10-25% w/w demethoxycurcumin and 25-45% w/w curcumin. In another related aspect, the curcuminoid composition comprises of 20-50% w/w bisdemethoxycurcumin, 10-25% w/w demethoxycurcumin and 30-50% w/w curcumin. In yet another related aspect, the total curcuminoids in the composition are in the range of 20-95% w/w. In a further related aspect, the composition further comprises of stabilizing agents, bioavailability enhancers and antioxidants, pharmaceutically or nutraceutically or cosmeceutically accepted excipients and enhancers and administered orally in the form of tablets, capsules, syrups, gummies, powders, suspensions, emulsions, chewables, candies or eatables.

In yet another related embodiment the bioavailability enhancer is selected from the group consisting of, but not limited to, piperine, quercetin, garlic extract, ginger extract, and naringin.

In another related aspect, one or more anti-oxidants and anti-inflammatory agents are selected from the group consisting of, but not limited to, vitamin A, D, E, K, C, B complex, rosmarinic acid, Alpha Lipoic Acid, Ellagic Acid, Glycyrrhizinic Acid, Epigallocatechin Gallate, plant polyphenols, Glabridin, moringa oil, olcanolic acid, Oleuropein, Carnosic acid, urocanic acid, phytoene, lipoid acid, lipoamide, ferritin, desferal, billirubin, billiverdin, melanins, ubiquinone, ubiquinol, ascorbyl palmitate, Mg ascorbyl phosphate, ascorbyl acetate, tocopherols and derivatives such as vitamin E acetate, uric acid, α-glucosylrutin, calalase and the superoxide dismutase, glutathione, selenium compounds, butylated hydroxyanisole (BHA), butylated hydroxytoluene (BHT), sodium metabisulfite (SMB), propyl gallate (PG) and amino acid cysteine.

In another most preferred embodiment, the invention discloses a method for the management of toxicity in mammalian kidney cells, said method comprising step of bringing into contact mammalian kidney cells with a composition comprising 20-80% w/w bisdemethoxycurcumin, 10-35% w/w demethoxycurcumin and 10-50% w/w curcumin, to reduce to toxic effects in the cells. In a further related aspect, the composition comprises of 30-70% bisdemethoxycurcumin, 10-25% w/w demethoxycurcumin and 30-50% w/w curcumin. In a further aspect, the composition comprises 40-60% bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 30-50% w/w curcumin. In yet another related aspect, the total curcuminoids in the composition are in the range of 20-95% w/w. In yet another related aspect, reduction in toxic effect in cells is brought about by preventing apoptosis and promoting autophagy. In another related aspect, the mammalian kidney cells are human cells.

In another most preferred embodiment, the invention discloses a method for the management of toxicity in mammalian kidney cells, said method comprising step of bringing into contact mammalian kidney cells with a curcuminoid composition comprising 20-80% w/w bisdemethoxycurcumin, 10-35% w/w demethoxycurcumin and 10-50% w/w curcumin and *Nigella sativa* extract standardised to contain not less than 2% w/w thymoquinone, about 0.01%-10% w/w thymohydroquinone, about 15%-95% w/w fatty acids, about 0.001%-3% w/w hederagenin or hederin, to reduce to toxic effects in the cells. In a further related aspect, the curcuminoid composition comprises of 30-70% bisdemethoxycurcumin, 10-25% w/w demethoxycurcumin and 30-50% w/w curcumin. In a further aspect, the curcuminoid composition comprises 40-60% bisdemethoxycurcumin, 10-25% w/w demethoxycurcumin and 30-50% w/w curcumin. In another related aspect, the curcuminoid composition comprises of 30-50% w/w bisdemethoxycurcumin, 10-25% w/w demethoxycurcumin and 30-50% w/w curcumin. In another related aspect, the curcuminoid composition comprises of 30-50% w/w bisdemethoxycurcumin, 10-25% w/w demethoxycurcumin and 25-45% w/w curcumin. In another related aspect, the curcuminoid composition comprises of 20-50% w/w bisdemethoxycurcumin, 10-25% w/w demethoxycurcumin and 25-45% w/w curcumin. In another related aspect, the curcuminoid composition comprises of 20-50% w/w bisdemethoxycurcumin, 10-25% w/w demethoxycurcumin and 30-50% w/w curcumin. In yet another related aspect, the total curcuminoids in the composition are in the range of 20-95% w/w. In yet another related aspect, reduction in toxic effect in cells is brought about by preventing apoptosis and promoting autophagy. In another related aspect, the mammalian kidney cells are human cells.

In another most preferred embodiment, the invention discloses a curcuminoid composition comprising 20-80% w/w bisdemethoxycurcumin, 10-35% w/w demethoxycurcumin and 10-50% w/w curcumin, for the management of toxicity in mammalian kidney cells. In a further related aspect, the composition comprises of 30-70% bisdemethoxycurcumin, 10-25% w/w demethoxycurcumin and 30-50% w/w curcumin. In a further aspect, the composition comprises 40-60% bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 30-50% w/w curcumin. In yet another related aspect, the total curcuminoids in the composition are in the range of 20-95% w/w. In yet another related aspect, reduction in toxic effect in cells is brought about by preventing apoptosis and promoting autophagy. In another related aspect, the mammalian kidney cells are human cells.

In another most preferred embodiment, the invention discloses a curcuminoid composition comprising 20-80% w/w bisdemethoxycurcumin, 10-35% w/w demethoxycurcumin and 10-50% w/w curcumin and *Nigella sativa* extract standardised to contain not less than 2% w/w thymoquinone, about 0.01%-10% w/w thymohydroquinone, about 15%-95% w/w fatty acids, about 0.001%-3% w/w hederagenin or hederin, for the management of toxicity in mammalian kidney cells. In a further related aspect, the curcuminoid composition comprises of 30-70% bisdemethoxycurcumin, 10-25% w/w demethoxycurcumin and 30-50% w/w curcumin. In a further aspect, the curcuminoid composition comprises 40-60% bisdemethoxycurcumin, 10-25% w/w demethoxycurcumin and 30-50% w/w curcumin. In another related aspect, the curcuminoid composition comprises of 30-50% w/w bisdemethoxycurcumin, 10-25% w/w demethoxycurcumin and 30-50% w/w curcumin. In another related aspect, the curcuminoid composition comprises of 30-50% w/w bisdemethoxycurcumin, 10-25% w/w demethoxycurcumin and 25-45% w/w curcumin. In another related aspect, the curcuminoid composition comprises of 20-50% w/w bisdemethoxycurcumin, 10-25% w/w demethoxycurcumin and 25-45% w/w curcumin. In another related aspect, the curcuminoid composition comprises of 20-50% w/w bisdemethoxycurcumin, 10-25% w/w demethoxycurcumin and 30-50% w/w curcumin. In yet another related aspect, the total curcuminoids in the composition are in the range of 20-95% w/w. In yet another related aspect, reduction in toxic effect in cells is brought about by preventing apoptosis and promoting autophagy. In another related aspect, the mammalian kidney cells are human cells.

In another most preferred embodiment, the invention discloses a method for the therapeutic management of nephrotoxicity in mammals, said method comprising step of administering an effective dose of a composition comprising 20-80% w/w bisdemethoxycurcumin, 10-35% w/w demethoxycurcumin and 10-50% w/w curcumin, to mammals with symptoms of nephrotoxicity to bring about nephroprotection. In a further related aspect, the composition comprises of 30-70% bisdemethoxycurcumin, 10-25% w/w demethoxycurcumin and 30-50% w/w curcumin. In a further aspect, the composition comprises 40-60% bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 30-50% w/w curcumin. In yet another related aspect, the total curcuminoids in the composition are in the range of 20-95% w/w. In another related aspect, the symptoms of nephrotoxicity include elevated urine albumin levels, decrease urine uric acid levels, elevated blood urea nitrogen levels and serum creatinine levels, anorexia, fatigue, mental status changes, nausea, vomiting, and pruritus. In yet another related aspect, nephroprotection is brought about by preventing apoptosis and promoting autophagy. In another related aspect, nephrotoxicity is induced by agents selected from the group consisting of drugs, ethylene glycol, carbon tetrachloride, sodium oxalate and heavy metals such as lead, mercury, cadmium and arsenic, biological agents such as viruses, mould and fungi, interferons, recombinant leukocytes and antibiotics. In yet another related aspect, the effective dose is in the range of 25-50 mg/kg bodyweight. In a related aspect, the therapeutic management is brought about by decreasing the elevated levels of serum and urine uric acid, urine albumin and blood urea nitrogen. In a related aspect, the therapeutic management is brought about by decreasing oxidative stress and inflammation. In a related aspect, the therapeutic management is brought about by preventing apoptosis and promoting autophagy. In a related aspect, the therapeutic management is brought about by decreasing the elevated levels of kidney injury markers selected from the group consisting of kidney injury molecule 1 (KIM 1), N-acetyl-β-D-glucosaminidase (NAG), and Neutrophil gelatinase-associated lipocalin (NGAL). In a related aspect, the therapeutic management is brought about by decreasing tubular necrosis, tubular interstitial fibrosis, cell necrosis and improving glomerular structure in the kidneys. In a further related aspect, the composition further comprises of stabilizing agents, bioavailability enhancers and antioxidants, pharmaceutically or nutraceutically or cosmeceutically accepted excipients and enhancers and administered orally in the form of tablets, capsules, syrups, gummies, powders, suspensions, emulsions, chewables, candies or eatables. In another related aspect, the mammal is human.

In another most preferred embodiment, the invention discloses a method for the therapeutic management of nephrotoxicity in mammals, said method comprising step of administering an effective dose of a composition comprising 20-80% w/w bisdemethoxycurcumin, 10-35% w/w demethoxycurcumin and 10-50% w/w curcumin and *Nigella sativa* extract standardised to contain not less than 2% w/w thymoquinone, about 0.01%-10% w/w thymohydroquinone, about 15%-95% w/w fatty acids, about 0.001%-3% w/w hederagenin or hederin, to mammals with symptoms of nephrotoxicity to bring about nephroprotection. In a further related aspect, the composition comprises of 30-70% bisdemethoxycurcumin, 10-25% w/w demethoxycurcumin and 30-50% w/w curcumin. In a further aspect, the composition comprises 40-60% bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 30-50% w/w curcumin. In yet another related aspect, the total curcuminoids in the composition are in the range of 20-95% w/w. In another related aspect, the symptoms of nephrotoxicity include elevated urine albumin levels, decrease urine uric acid levels, elevated blood urea nitrogen levels and serum creatinine levels, anorexia, fatigue, mental status changes, nausea, vomiting, and pruritus. In yet another related aspect, nephroprotection is brought about by preventing apoptosis and promoting autophagy. In another related aspect, nephrotoxicity is induced by agents selected from the group consisting of drugs, ethylene glycol, carbon tetrachloride, sodium oxalate and heavy metals such as lead, mercury, cadmium and arsenic, biological agents such as viruses, mould and fungi, interferons, recombinant leukocytes and antibiotics. In yet another related aspect, the effective dose is preferably in the range of 25 to 50 mg/kg bodyweight, or more preferably in the range of 30 to 50 mg/kg bodyweight, or more preferably in the range of 30 to 40 mg/kg bodyweight. In a related aspect, the therapeutic management is brought about by decreasing the elevated levels of serum and urine uric acid, urine albumin and blood urea nitrogen. In a related aspect, the therapeutic management is brought about by decreasing oxidative stress and inflammation. In a related aspect, the therapeutic management is brought about by preventing apoptosis and promoting autophagy. In a related aspect, the therapeutic management is brought about by decreasing the elevated levels of kidney injury markers selected from the group consisting of kidney injury molecule 1 (KIM 1), N-acetyl-β-D-glucosaminidase (NAG), and Neutrophil gelatinase-associated lipocalin (NGAL). In a related aspect, the therapeutic management is brought about by decreasing tubular necrosis, tubular interstitial fibrosis, cell necrosis and improving glomerular structure in the kidneys. In a further related aspect, the composition further comprises of stabilizing agents, bioavailability enhancers and antioxidants, pharmaceutically or nutraceutically or cosmeceutically accepted excipients and enhancers and administered orally in the form of tablets, capsules, syrups, gummies, powders, suspensions, emulsions, chewables, candies or eatables. In another related aspect, the mammal is human.

In another most preferred embodiment, the invention discloses a composition comprising 20-80% w/w bisdemethoxycurcumin, 10-35% w/w demethoxycurcumin and 10-50% w/w curcumin for the therapeutic management of nephrotoxicity in mammals. In a further related aspect, the composition comprises of 30-70% bisdemethoxycurcumin, 10-25% w/w demethoxycurcumin and 30-50% w/w curcumin. In a further aspect, the composition comprises 40-60% bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 30-50% w/w curcumin. In yet another related aspect, the total curcuminoids in the composition are in the range of 20-95% w/w. In another related aspect, the symptoms of nephrotoxicity include elevated urine albumin levels, decrease urine uric acid levels, elevated blood urea nitrogen levels and serum creatinine levels, anorexia, fatigue, mental status changes, nausea, vomiting, and pruritus. In yet another related aspect, nephroprotection is brought about by preventing apoptosis and promoting autophagy. In another related aspect, nephrotoxicity is induced by agents selected from the group consisting of drugs, ethylene glycol, carbon tetrachloride, sodium oxalate and heavy metals such as lead, mercury, cadmium and arsenic, biological agents such as viruses, mould and fungi, interferons, recombinant leukocytes and antibiotics. In yet another related aspect, the effective dose is in the range of 25-50 mg/kg bodyweight. In a related aspect, the therapeutic management is brought about by decreasing the elevated levels of serum and urine uric acid, urine albumin and blood urea nitrogen. In a related aspect, the therapeutic management is brought about by decreasing oxidative stress and inflammation. In a related aspect, the therapeutic management is brought about by preventing apoptosis and promoting autophagy. In a related aspect, the therapeutic management is brought about by decreasing the elevated levels of kidney injury markers selected from the group consisting of kidney injury molecule 1 (KIM 1), N-acetyl-β-D-glucosaminidase (NAG), and Neutrophil gelatinase-associated lipocalin (NGAL). In a related aspect, the therapeutic management is brought about by decreasing tubular necrosis, tubular interstitial fibrosis, cell necrosis and improving glomerular structure in the kidneys. In a further related aspect, the composition further comprises of stabilizing agents, bioavailability enhancers and antioxidants, pharmaceutically or nutraceutically or cosmeceutically accepted excipients and enhancers and administered orally in the form of tablets, capsules, syrups, gummies, powders, suspensions, emulsions, chewables, candies or eatables. In another related aspect, the mammal is human.

In another most preferred embodiment, the invention discloses a composition comprising 20-80% w/w bisdemethoxycurcumin, 10-35% w/w demethoxycurcumin and 10-50% w/w curcumin and *Nigella sativa* extract standardised to contain not less than 2% w/w thymoquinone, about 0.01%-10% w/w thymohydroquinone, about 15%-95% w/w fatty acids, about 0.001%-3% w/w hederagenin or hederin for the therapeutic management of nephrotoxicity in mammals. In a further related aspect, the composition comprises of 30-70% bisdemethoxycurcumin, 10-25% w/w demethoxycurcumin and 30-50% w/w curcumin. In a further aspect, the composition comprises 40-60% bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 30-50% w/w curcumin. In another related aspect, the composition comprises of 30-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 25-45% w/w curcumin. In another related aspect, the composition comprises of 20-50% w/w bisdemethoxycurcumin, 10-25% w/w demethoxycurcumin and 30-50% w/w curcumin. In yet another related aspect, the total curcuminoids in the composition are in the range of 20-95% w/w. In another related aspect, the symptoms of nephrotoxicity include elevated urine albumin levels, decrease urine uric acid levels, elevated blood urea nitrogen levels and serum creatinine levels, anorexia, fatigue, mental status changes, nausea, vomiting, and pruritus. In yet another related aspect, nephroprotection is brought about by preventing apoptosis and promoting autophagy. In another related aspect, nephrotoxicity is induced by agents selected from the group consisting of drugs, ethylene glycol, carbon tetrachloride, sodium oxalate and heavy metals such as lead, mercury, cadmium and arsenic, biological agents such as viruses, mould and fungi, interferons, recombinant leukocytes and antibiotics. In yet another related aspect, the effective dose is in the range of 25 to 50 mg/kg bodyweight, or more preferably in the range of 30 to 50 mg/kg bodyweight, or more preferably in the range of 30 to 40 mg/kg bodyweight. In a related aspect, the therapeutic management is brought about by decreasing the elevated levels of serum and urine uric acid, urine albumin and blood urea nitrogen. In a related aspect, the therapeutic management is brought about by decreasing oxidative stress and inflammation. In a related aspect, the therapeutic management is brought about by preventing apoptosis and promoting autophagy. In a related aspect, the therapeutic management is brought about by decreasing the elevated levels of kidney injury markers selected from the group consisting of kidney injury molecule 1 (KIM 1), N-acetyl-β-D-glucosaminidase (NAG), and Neutrophil gelatinase-associated lipocalin (NGAL). In a related aspect, the therapeutic management is brought about by decreasing tubular necrosis, tubular interstitial fibrosis, cell necrosis and improving glomerular structure in the kidneys. In a further related aspect, the composition further comprises of stabilizing agents, bioavailability enhancers and antioxidants, pharmaceutically or nutraceutically or cosmeceutically accepted excipients and enhancers and administered orally in the form of tablets, capsules, syrups, gummies, powders, suspensions, emulsions, chewables, candies or eatables. In another related aspect, the mammal is human.

Specific illustrative examples enunciating the most preferred embodiments are included herein below.

EXAMPLES

Example 1: Composition

The composition comprising 20-80% w/w bisdemethoxycurcumin, 10-35% w/w demethoxycurcumin and 10-50% w/w curcumin was isolated from a selected variety of *Curcuma longa*. Generally, the content of bisdemethoxycurcumin occurs in the range of 5-20% w/w in most rhizomes of *Curcuma longa*. However, increased concentrations of bisdemethoxycurcumin was isolated and enriched from selected variety of *Curcuma longa* using the following steps:

a. Extracting the turmeric raw material using organic solvent in a quantity of 3-5 times the volumes of raw material, under a controlled temperature of 50-70° C. with constant stirring for 2-3 hours to yield a filtrate,
b. Repeating the process of step a) to yield a filtrate and marc of turmeric,
c. Extracting the marc of step b) with organic solvent in a quantity of 3-5 times the volumes of marc at a temperature of 55-80° C., to obtain a filtrate
d. Repeating the process of step c) 3-4 times and pooled the filtrate to obtain a turmeric oleoresin with 10-25% w/w BDMC, 8-20% w/w DMC and Curcumin 10-25% w/w, wherein the total Curcuminoids content is 30-60% w/w by HPLC.
e. Crystallizing the oleoresin of step d) with a mixture organic solvents at 0-5° C. for 3-4 hours,
f. Filtering under vacuum at a temperature of 20-30° C., to obtain a residue and a filtrate,
g. Drying the residue of step f), to obtain a dry powder
h. Reducing the volume of filtrate of step f) to half and recrystallizing using organic solvent at 20-30° C. overnight,
i. Filtering and drying the crystals to obtain a crystalline powder
j. Blended the fractions of step g) and i) to obtain a composition comprising Curcumin—24-45%; demethoxycurcumin—10-25% and bisdemethoxycurcumin—20-50% w/w.

The solvent of step a) can be selected from the group consisting of hexane, heptane, petroleum ether. The solvent of step c), e) and h) can be selected from the group consisting of acetic acid, acetone, ethanol, ethyl acetate, hexane, heptane, isopropanol, methanol, n-Propanol, pentane, toluene, water or combinations thereof. The above mentioned ratios are merely illustrative and a person skilled in the art will be able to arrive at the a composition comprising 20-50% w/w bisdemethoxycurcumin, 10-25% w/w demethoxycurcumin and 25-50% w/w curcumin by alerting the ratios of the fractions.

The composition comprising 20-80% w/w bisdemethoxycurcumin, 10-35% w/w demethoxycurcumin and 10-50% w/w curcumin can also be isolated from residual material of turmeric rhizomes using processes available in scientific literature.

The actives from *Nigella sativa* (NS extract) were isolated and standardised using a process disclosed in US 2019-0192447.

In addition to *Nigella sativa* extract, the composition comprising 20-80% w/w bisdemethoxycurcumin, 10-35% w/w demethoxycurcumin and 10-50% w/w curcumin can also be added to/mixed with other plant ingredients and compositions and evaluated for its nephroprotective potential.

Example 2—In Vitro Nephroprotective Effects of Composition

The invitro nephroprotective effects were evaluated in Cisplatin induced Nephrotoxicity model in Human embryonic kidney cells (HEK293).

Treatment with cisplatin induces toxicity in the cells by elevating oxidative stress and inflammation via the NFκB pathway. This activates the pro-apoptotic BAX and Caspase 3 and promotes cell death. Induction of autophagy in cisplatin treated cells is reported to rescue the cells from apoptosis (Takahashi et al., Autophagy Guards Against Cisplatin-Induced Acute Kidney Injury, A J P, 2012; 180(2): 517-525).

In the present invention the nephroprotective potential of a composition comprising 20-80% w/w bisdemethoxycurcumin, 10-35% w/w demethoxycurcumin and 10-50% w/w curcumin (preferably in the range of 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin.)—AC3 complex was tested. The specific rage of the composition used in the experiment include 32% w/w bisdemethoxycurcumin, 25% demethoxycurcumin and 38% curcumin (total curcuminoids content: 22%). It is to be noted that the range tested is merely illustrative and the results are application to the aforementioned ranges of the composition. The nephroprotective role of the composition was evaluated by the accessing the protective effect via the MTT assay and ROS levels.

Nephroprotection—(MTT method): HEK-293 cells were seeded into a microtiter plate at a density of 104 cells/well and allowed to adhere overnight. Cells with indicated concentrations of the composition were treated with 12.5 UM of cisplatin for 24 h, and grown in 5 mg/ml MTT at 37° C. Four hour later, 200 µl of solubilization solution was added to each well and absorption values read at 570 nm on Tecan microtiter plate reader. Data were expressed as the mean percent of viable cells vs. control.

Antioxidant assay (ROS): HEK-293 (5×104 cells/well) cells were incubated with Cisplatin (120 µM) and treated with different concentrations the composition in DMEM 1% FBS for 18 hr. Cells were treated with 1 µM DCFDA and incubated at 37° C. for 30 minutes in dark. The fluorescence was recorded at excitation and emission wavelengths of 485 and 520 nm (FLUOStar Optima, Ortenberg, Germany). The percentage of ROS scavenging was calculated to the fluorescence intensity of Cisplatin treated control cells.

Figure 2:
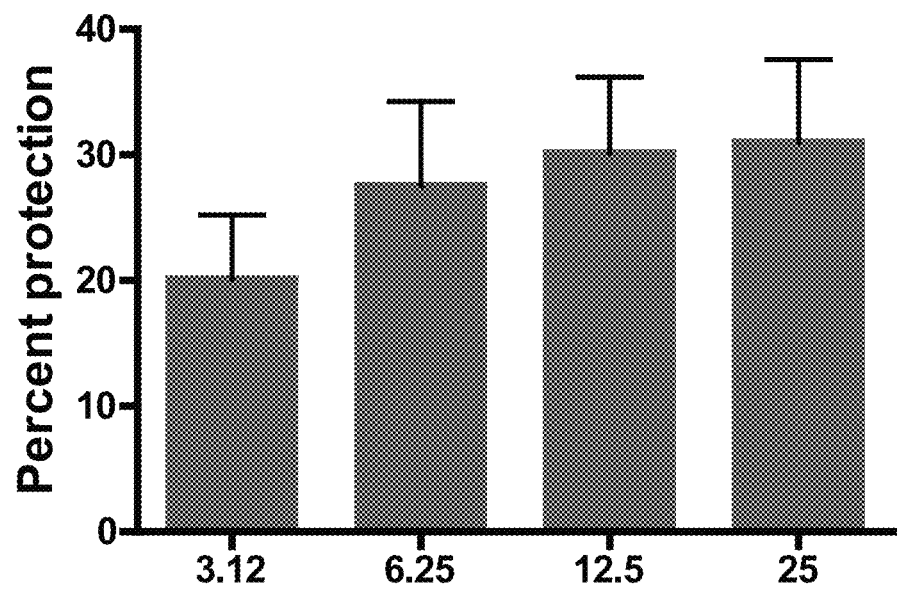
FIG. 2 is a graphical representation showing the protection of cells against ROS using a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin.

The results indicated that the AC3 complex protected the kidneys against damage (FIG. 1) and ROS (FIG. 2).

Figure 3:
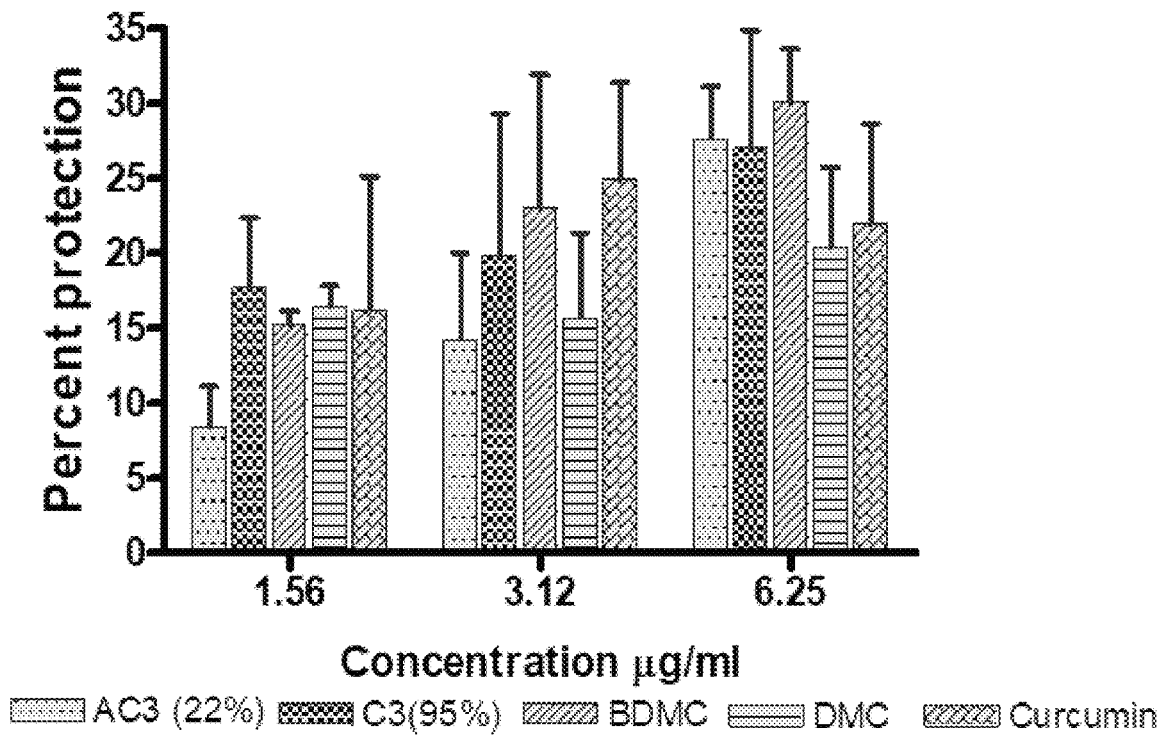
FIG. 3 is a graphical representation showing the nephroprotective effects (MTT assay) of a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, compared with 95% w/w bisdemethoxycurcumin (BDMC), 95% w/w curcumin and composition enriched in curcumin (95% curcuminoids) which comprises 75-81% curcumin, 15-19% demethoxycurcumin, and 2.2-6.5% bisdemethoxycurcumin.
Figure 4:
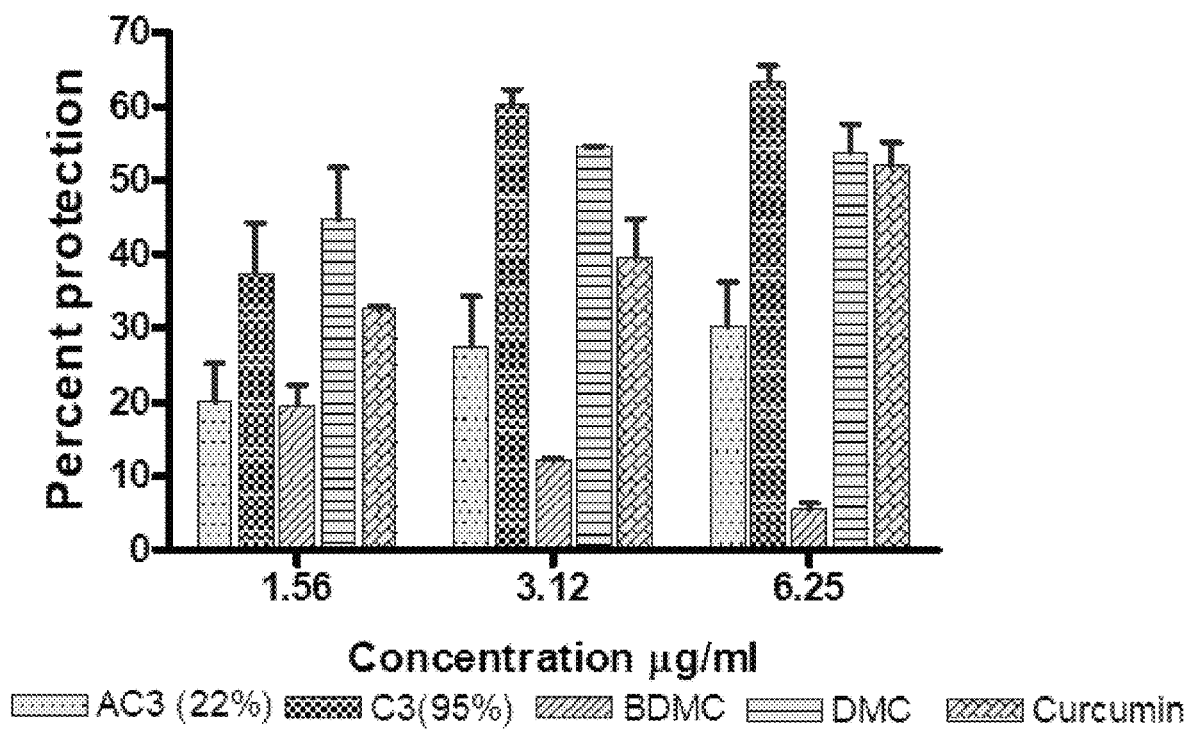
FIG. 4 is a graphical representation showing the protection of cells against ROS using a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, compared with 95% w/w bisdemethoxycurcumin (BDMC), 95% w/w curcumin and composition enriched in curcumin (95% curcuminoids) which comprises 75-81% curcumin, 15-19% demethoxycurcumin, and 2.2-6.5% bisdemethoxycurcumin.

The AC3 composition was compared with 95% w/w bisdemethoxycurcumin (BDMC), 95% w/w curcumin and composition enriched in curcumin (95% curcuminoids) which comprises 75-81% curcumin, 15-19% demethoxycurcumin, and 2.2-6.5% bisdemethoxycurcumin—C3 complex. The results are provided in FIG. 3 (Cell protection) and FIG. 4 (ROS protection). It is to be noted that the total curcuminoid content in the sample tested is only 22% w/w which when compared to 95% w/w of individual extracts, showed comparatively much better protection and is to be considered synergistic.

Figure 5:
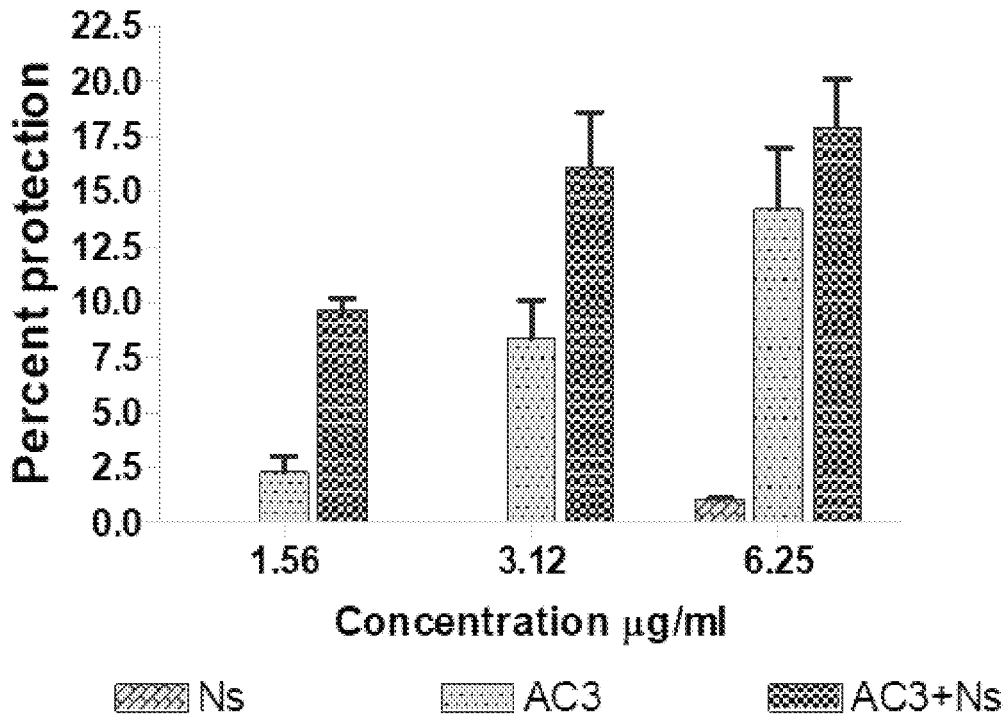
FIG. 5 is a graphical representation showing the nephroprotective effects (MTT assay) of a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin and Nigella sativa extract, individually and in combination.
Figure 6:
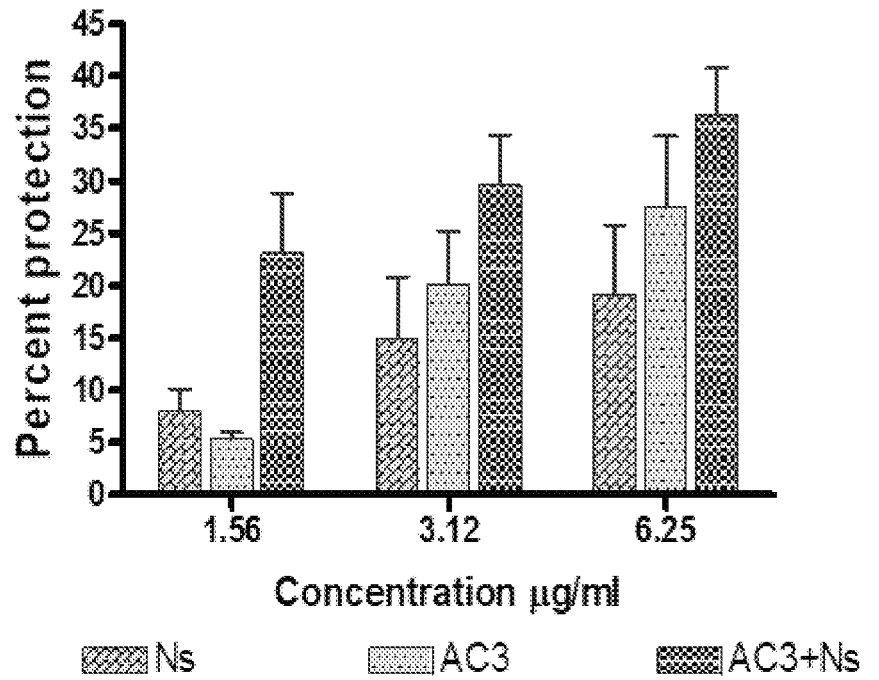
FIG. 6 is a graphical representation showing the protection of cells against ROS using a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination.

The nephroprotective effect of AC3 complex was also tested along with *Nigella sativa* extract (NS). It was observed that the composition comprising AC3 complex and NS extract was much better in protecting the cells against damage (FIG. 5) and ROS (FIG. 6).

The apoptotic and autophagy markers were estimated using qRT-PCR. RNA was extracted from HEK293 cells using the trizol method. First-strand cDNA was prepared using RevertAid first strand cDNA synthesis kit (thermoscientific). Quantitative real-time PCR (qRT-PCR) was performed with SYBR Green I fluorescent dye using Light cycler 96 according to the manufacturer's instructions (Light Cycler® FastStart DNA Master SYBR Green I, Roche). Expression levels for all genes were normalized to β-actin gene. The following primers were used for the analysis.

TABLE 1

List of primers

| Name | Primer sequence (Forward) | Primer sequence (Reverse) |
| --- | --- | --- |
| h BAX | TCAGGATGCGTCCAC CAAGAAG (SEQ ID NO: 1) | TGTGTCCACGGCGGC AATCATC (SEQ ID NO: 2) |
| h Bcl-2 | GAG TAC CTG AAC CGG CAT CT (SEQ ID NO: 3) | GAA ATC AAA CAG AGG TCG CA (SEQ ID NO: 4) |
| h LC3B | GAGAAGCAGCTTCCT GTTCTGG (SEQ ID NO: 5) | GTGTCCGTTCACCAA CAGGAAG (SEQ ID NO: 6) |
| β-actin | CCCGCGAGTACAACC TTCT (SEQ ID NO: 7) | CGTCATCCATGGCGA ACT (SEQ ID NO: 8) |

Figure 7:
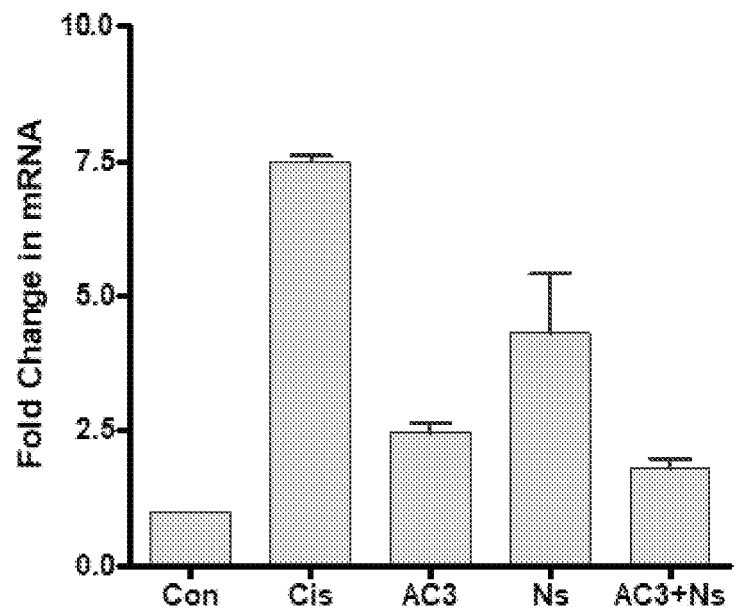
FIG. 7 is a graphical representation showing the decrease in levels of pro-apoptotic marker BAX by composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination.
Figure 8:
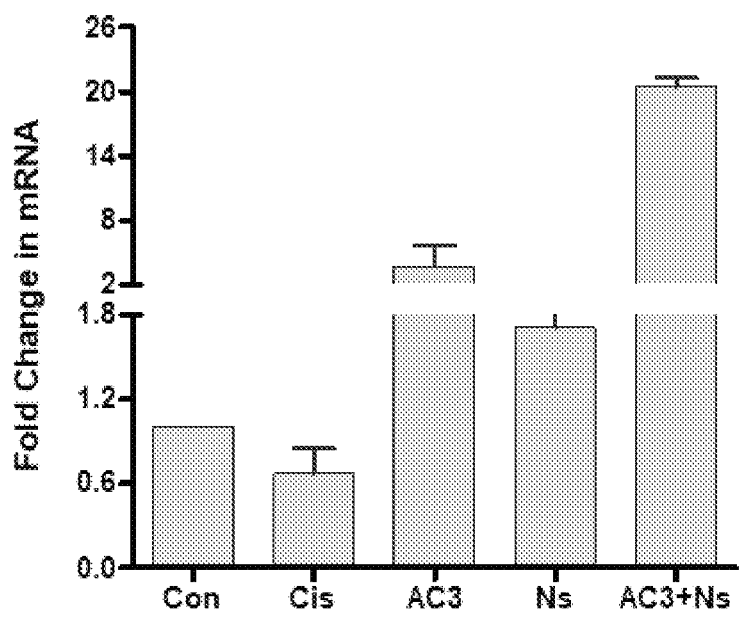
FIG. 8 is a graphical representation showing the increase in levels of anti-apoptotic marker BCL-2 by composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination.
Figure 9:
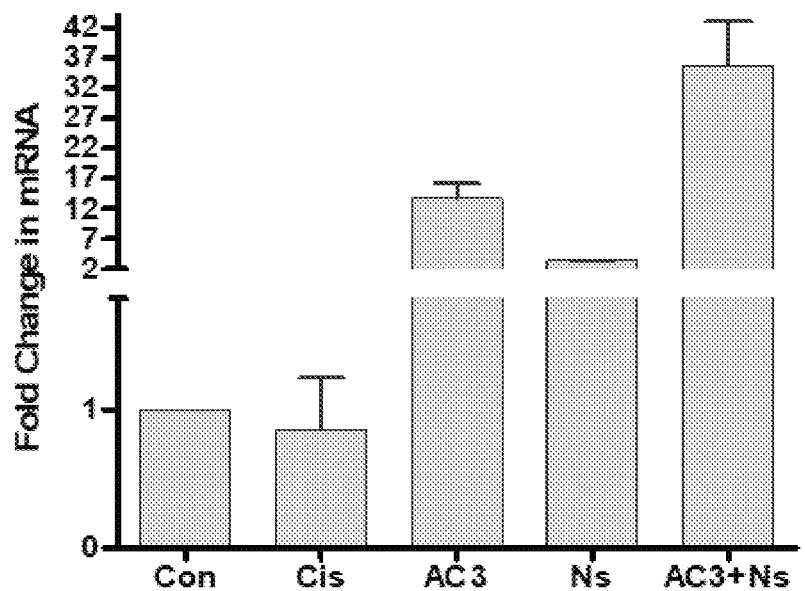
FIG. 9 is a graphical representation showing the increase in levels of autophagy marker LC-3b by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination.

The composition comprising AC3 complex and NS extract also showed much better effect in decreasing the pro-apoptotic marker BAX (FIG. 7) and increasing anti-apoptotic marker BCL-2 (FIG. 8) and autophagy marker LC-3b (FIG. 9).

Example 3—In Vivo Nephroprotective Effects

Methodology:

Animals and Experimental design: Animals were housed under standard air-conditioned laboratory conditions. The temperature was maintained at maximum: 24° C. and a minimum of 23° C. and Relative humidity at maximum: 63% and a minimum of 48% with 12 h light and 12 h dark cycle. The maximum and minimum temperature and relative humidity in the experimental room were recorded once daily. The male SD rats were randomized into eight groups of seven animals. The test substances were administered for 15 days. The cisplatin (7 mg/kg) was administered on 10th day through intraperitoneal injection. On 16th day all the animals were sacrificed to collect blood and organs for biochemistry and histopathology respectively. The experiment was carried out in accordance with the guidelines for animal experimentation of the control for Committee for the Purpose of Control and Supervision of Experiments on Animals (CPCSEA), India with the approval from the Institutional animal ethics committee. Experiments were performed to access the levels of oxidative stress, apoptosis, inflammation, kidney injury markers, creatinine, uric acid and BUN levels, serum calcium and phosphorus along with histopathological examination to access the tubular necrosis, glomerular structure, tubular interstitial fibrosis and necrosis.

Biochemical Markers

Urine Albumin, serum creatinine, serum and urine uric acid, BUN were measured as per manufacturer's instructions (Robonik, Prietest) and analysed by Robonic Biochemical analyzer. Level of Phosphorus was detected as per kit method (Accucare phosphorus UV molybate method). Calcium levels were estimated using a calcium testing kit (Prietest, Robonik, India)

Figure 10:
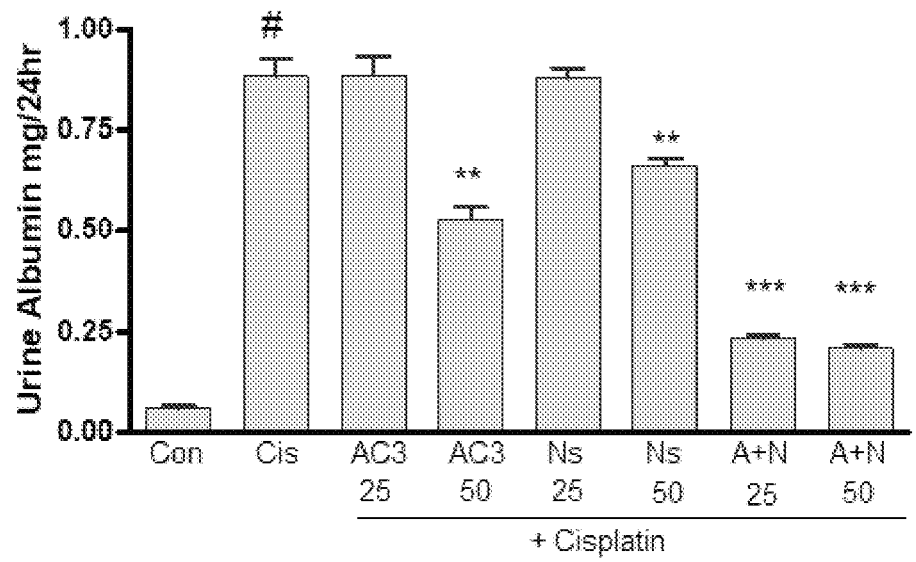
FIG. 10 is a graphical representation showing the decrease in urine albumin levels in experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination.  $P<0.01$, * $P<0.001$

Urine albumin levels are established as a marker for accessing acute kidney injury (Bolisetty et al. Urine albumin as a biomarker in acute kidney injury, Am J Physiol Renal Physiol. 2011; 300(3): F626-F627). Albumin is a major protein normally present in blood Virtually no albumin is present in the urine when the kidneys are functioning properly. The presence of Albumin in urine signified kidney damage. In the study, urine albumin levels were significantly reduced by the AC3 complex and NS extract at 50 mg/kg. The combination comprising AC3 and NS extract was highly effective compared to individual treatment (FIG. 10).

Figure 11:
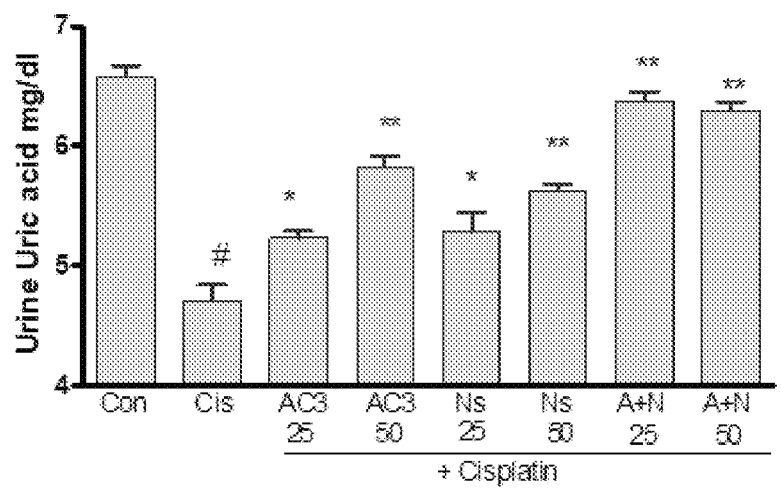
FIG. 11 is a graphical representation showing the increase in urine uric acid levels in experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination. * $P<0.05$, ** $P<0.01$.

Serum and urine uric acid levels are an indicator for the development of kidney disease and acute kidney injury (Giordano et al., Uric Acid as a Marker of Kidney Disease: Review of the Current Literature, Disease Markers, Volume 2015, Article ID 382918, 6 pages). Low uric acid levels in urine indicate kidney disease that impairs the kidneys' ability to get rid of uric acid. In the present study, uric acid levels were low in urine due to cisplatin induced toxicity. Treatment of AC 3 complex and NS extract restored the uric acid levels and the combination of AC 3 and NS extract was highly effective in restoring the decreased urine uric acid levels (FIG. 11)

Figure 12:
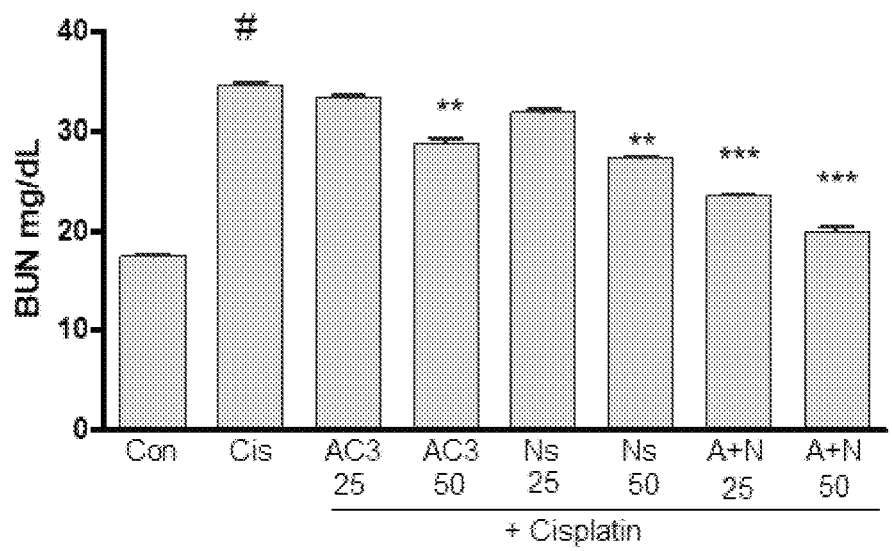
FIG. 12 is a graphical representation showing the decrease in blood urea nitrogen levels in experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination.  $P<0.01$, * $P<0.001$

Blood urea nitrogen (BUN) test measures the amount of nitrogen in the blood that comes from urea. If kidneys are not able to remove urea from the blood normally, BUN level rises. Many conditions like Heart failure, dehydration, or a diet high in protein can also increase BUN. In the present investigation BUN levels were increased with cisplatin and the levels were significantly reduced by the AC3 complex and NS extract at 50 mg/kg. The combination comprising AC3 complex and NS extract was much effective in reducing BUN levels (FIG. 12)

Figure 13:
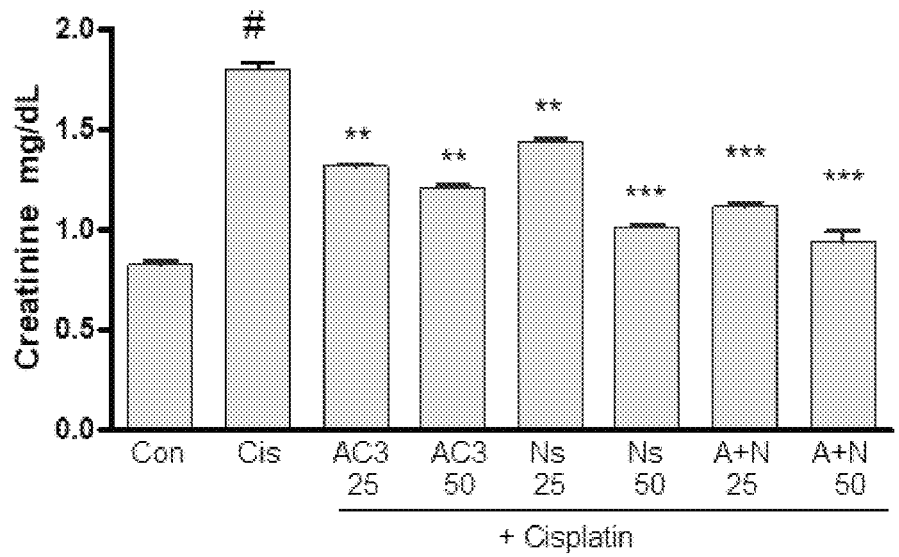
FIG. 13 is a graphical representation showing the decrease in serum creatinine levels in experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination.  $P<0.01$, * $P<0.001$

Elevated creatinine level signifies impaired kidney function. Generally, creatinine is removed from body primarily by glomerular filtration, and by proximal tubular secretion. Increase in serum creatinine levels signified impaired filtration. In the present study, cisplatin administration significantly increased serum creatinine levels. Administration of AC3 complex and NS extract, effectively reduced the serum creatinine levels (FIG. 13)

Figure 14:
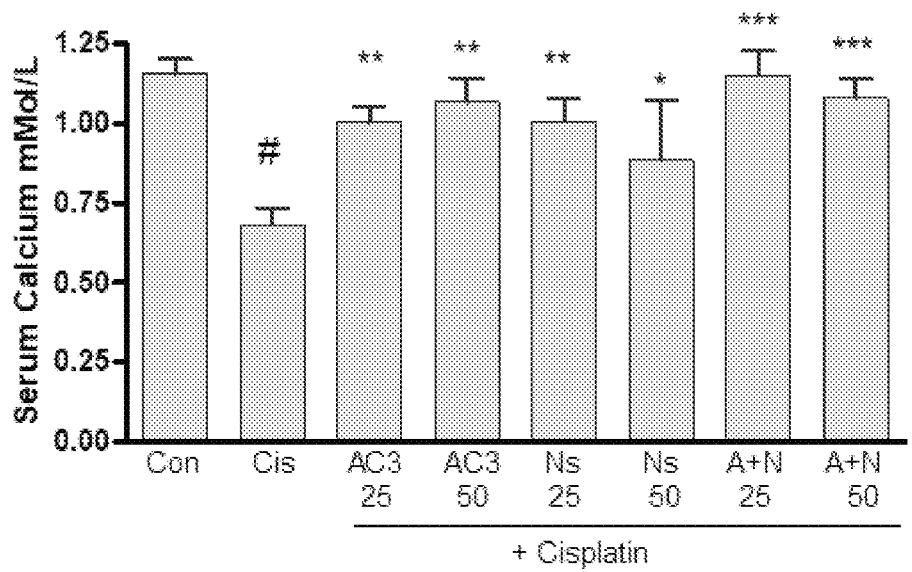
FIG. 14 is a graphical representation showing the increase in serum calcium levels in experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination. * $P<0.05$,  $P<0.01$, * $P<0.001$
Figure 15:
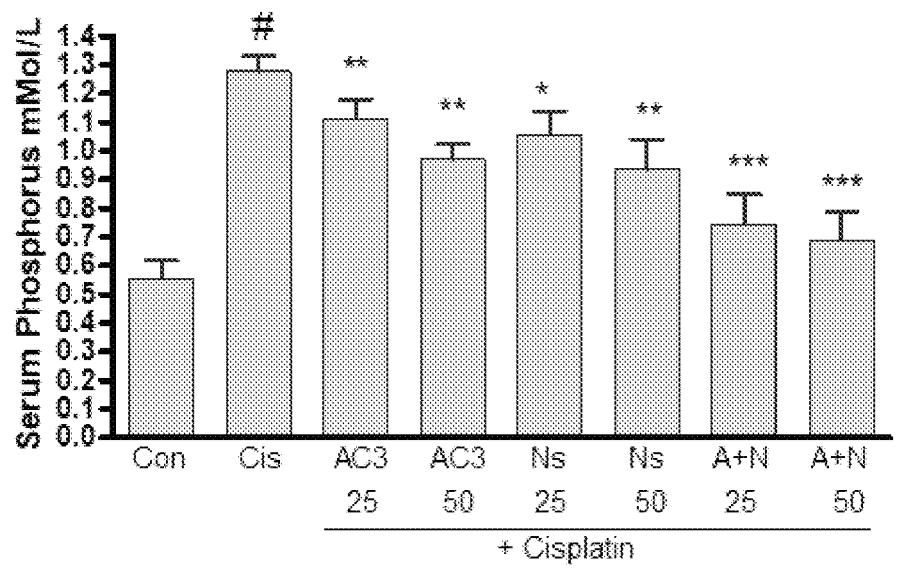
FIG. 15 is a graphical representation showing the decrease in serum phosphorus levels in experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination. * $P<0.05$,  $P<0.01$, * $P<0.001$.

Similarly, Cisplatin administration lowers the circulating calcium levels and increases phosphorus levels. Mechanistically, vitamin D is converted to its to its biologically active form, 1,25D, in the kidneys, immune cells, and other tissues by CYP27B1. Cisplatin decreases renal synthesis of 1,25D, which results in decreased calcium absorption from the gut, decreased calcium reabsorption from the kidneys, and decreased calcium release from bone. Hyperphosphatemia, also decreases total serum calcium levels via sequestration of calcium in the circulation. In the present study, calcium (FIG. 14) and phosphorus levels (FIG. 15) were normalized by AC3 and NS extract with the combination showing much better effect.

Biomarkers of Kidney Injury

The levels of kidney injury molecule 1 (KIM 1), N-acetyl-β-D-glucosaminidase (NAG), and Neutrophil gelatinase-associated lipocalin (NGAL) were assessed. NGAL (RayBio-1120200745, USA) and NAG (BioVision-K733-100, USA) were measured from urine according to the manufacturer's instruction. KIM-1 (RayBio-1120200751, USA) from urine was carried as per kit method.

Figure 16:
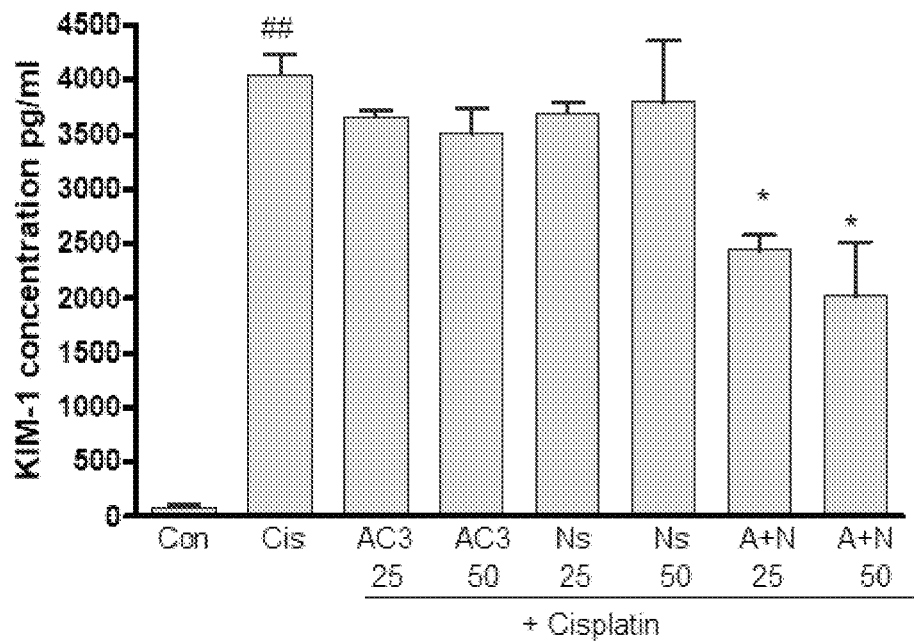
FIG. 16 is a graphical representation showing the decrease in kidney injury molecule-1 levels in experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination. * $P<0.05$.

Kidney injury molecule 1 (KIM-1) is a promising marker for early detection of AKI (Tanase et al., The Predictive Role of the Biomarker Kidney Molecule-1 (KIM-1) in Acute Kidney Injury (AKI) Cisplatin-Induced Nephrotoxicity, Int J Mol Sci. 2019; 20(20): 5238). The concentration of KIM increases rapidly within hours following kidney injury. In general KIM-1 expression is low in normal kidneys but is significantly increased in proximal tubule cells following acute kidney injury. Plasma and urinary KIM-1 levels are reported to be significantly elevated in both kidney injury and choric kidney disease patients (Tian et al., Kidney Injury Molecule-1 is Elevated in Nephropathy and Mediates Macrophage Activation via the Mapk Signalling Pathway, Cell Physiol Biochem 2017; 41:769-783). In the present study, KIM-1 levels were significantly high in cisplatin injured rats. Combination of AC3 and NS extract was highly effective in reducing KIM-1 levels (FIG. 16).

Figure 17:
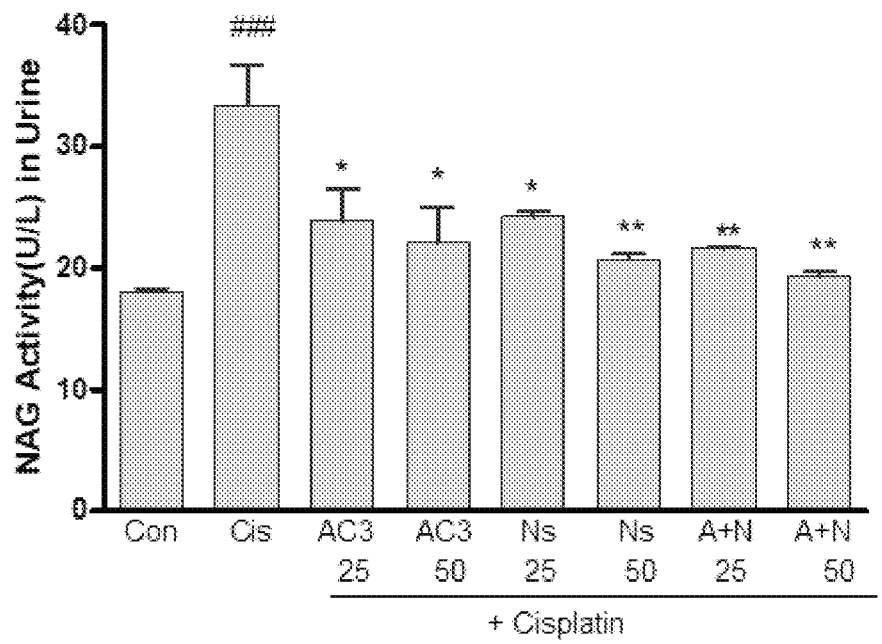
FIG. 17 is a graphical representation showing the decrease in urinary N-acetyl-β-D-glucosaminidase levels in experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination. * $P<0.05$, ** $P<0.01$.

Urinary N-acetyl-β-D-glucosaminidase (NAG), a marker of proximal tubular damage, is a lysosomal brush-border enzyme of 140 kda that breaks down glycoproteins in the proximal tubules where it is mainly expressed (Parikh et al., Tubular proteinuria in acute kidney injury: a critical evaluation of current status and future promise, Ann Clin Biochem 2010; 47: 301-312. DOI: 10.1258/acb.2010.010076). Plasma levels of NAG are normally not filtered by the glomeruli and its excretion into urine correlates with tubular cell injury. Abnormally high levels of NAG are detected in kidney diseases including diabetic nephropathy, glomerulonephritis, tubulointerstitial diseases, renal allograft rejection, and toxic renal injury (Liangos et al., Urinary N-Acetyl-β-(D)-Glucosaminidase Activity and Kidney Injury Molecule-1 Level Are Associated with Adverse Outcomes in Acute Renal Failure, March 2007, 18 (3) 904-912). In the present investigation, cisplatin administration elevated NAG levels which were normalized by the administration of AC3 complex and NS extract (FIG. 17)

Figure 18:
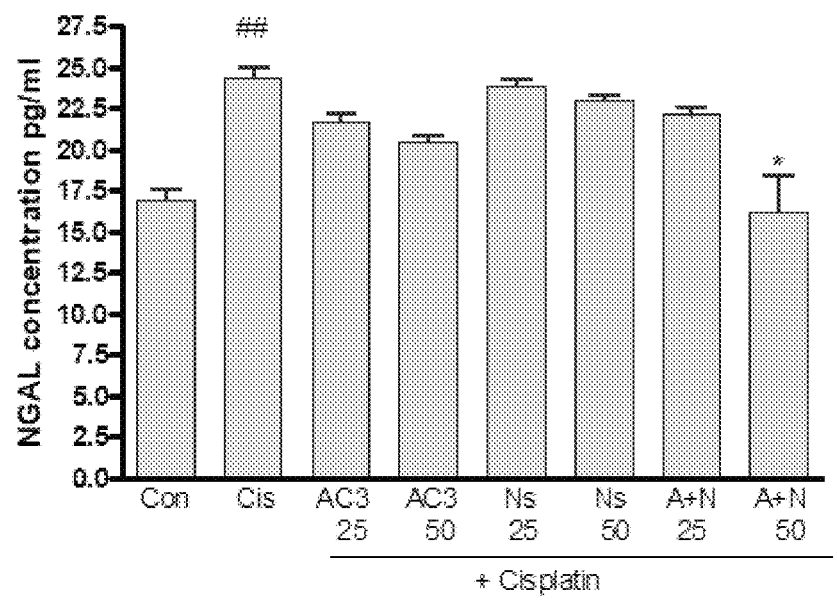
FIG. 18 is a graphical representation showing the decrease in Neutrophil gelatinase-associated lipocalin levels in experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination. * $P<0.05$.

Neutrophil gelatinase-associated lipocalin (NGAL) is a 25-kd protein initially identified bound to gelatinase in specific granules of the neutrophil. It is expressed in various tissues at low levels, and is induced in epithelial cells upon inflammation or injury. Elevated NGAL levels are predictive of poor clinical outcomes in AKI, including dialysis initiation and mortality, even when adjusted for conventional predictors, such as creatinine levels. Significant reduction in NGAL was observed in AC3 and NS treated animals (FIG. 18).

Markers of Oxidative Stress and Inflammation

The presence of oxidative stress and inflammation was assessed by evaluating the levels of Nuclear factor erythroid 2-related factor 2 (Nrf2), NF-κB, superoxide dismutase enzyme, lipid peroxidation (malondialdehyde—MDA), IL-1β, IL-6, TNF-α and IFN-γ levels/expression in the kidney.

Nuclear factor erythroid 2-related factor 2 (Nrf2) is a key transcriptional regulator for the protection of cells against oxidative and xenobiotic stresses. It plays a critical role in the mitigating the effect of acute kidney damage (Rubio-Navarro et al., Nrf2 Plays a Protective Role Against Intravascular Hemolysis-Mediated Acute Kidney Injury, Front. Pharmacol. 10:740. doi: 10.3389/fphar.2019.00740). Cisplatin administration decreases Nrf2 leading apoptosis and renal injury.

Similarly, NF-κB induces the production of pro-inflammatory factors, such as IL-1β and TNF-α. The levels of NF-κB is elevated in cisplatin induced renal injury.

In the present investigation, their levels were evaluated using western blotting. The kidney tissue (50 mg) was ground in liquid nitrogen into a powder using a mortar and pestle and transferred to ice-cold RIPA buffer containing protease inhibitor cocktail (HiMedia, India) and phosphatase (sodium orthovanadate 1 mM). Proteins were extracted with constant agitation for 2 h at 4° C., and their concentration was estimated by the BCA method. Cellular protein (80 µg) was loaded per lane in denatured 10% polyacrylamide gel (SDS-PAGE), transferred to a polyvinylidene difluoride membrane (Invitrolon™ PVDF, Thermo Fisher Scientific, USA) and blocked in 5% non-fat dry milk for 2 h. Membranes were then incubated with the appropriate dilutions of primary antibodies against Nrf-2 p-NFkb, and β-actin for 18 h at 4° C. and horseradish peroxidase-conjugated secondary antibody for 2 h at 37° C. Immunoreactive protein bands were detected by ECL (Pierce ECL plus, Thermo Scientific, USA). Immunoblots were quantified using Image J software (version 1.52a, National Institute of Health, USA).

Figure 19:
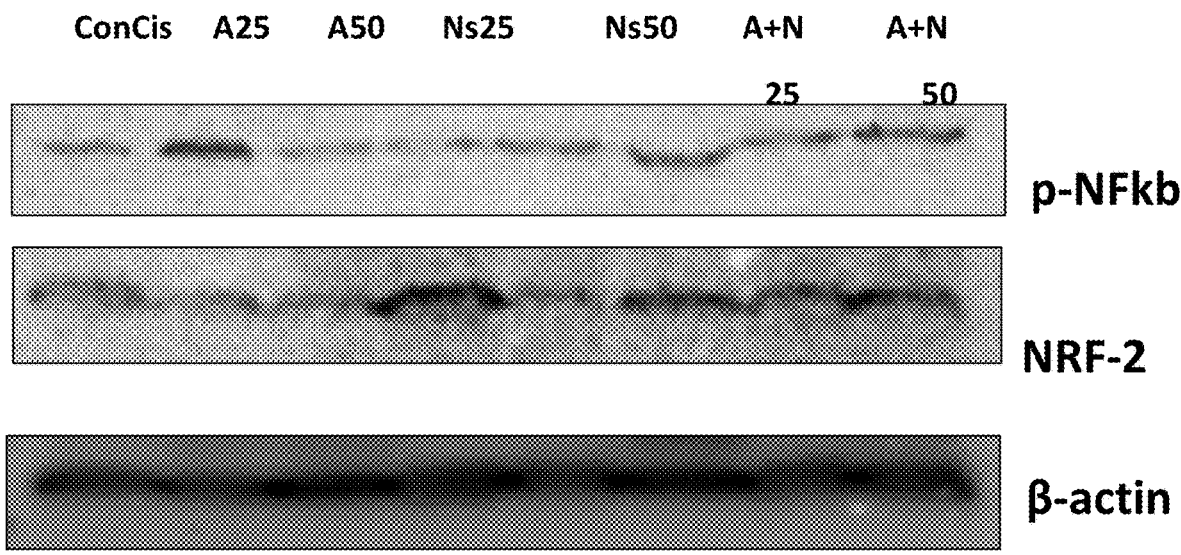
FIG. 19 is a western blot image showing the increase in the expression of NRF2 levels and decrease in the expression of NFκB in kidneys of experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination.
Figure 20:
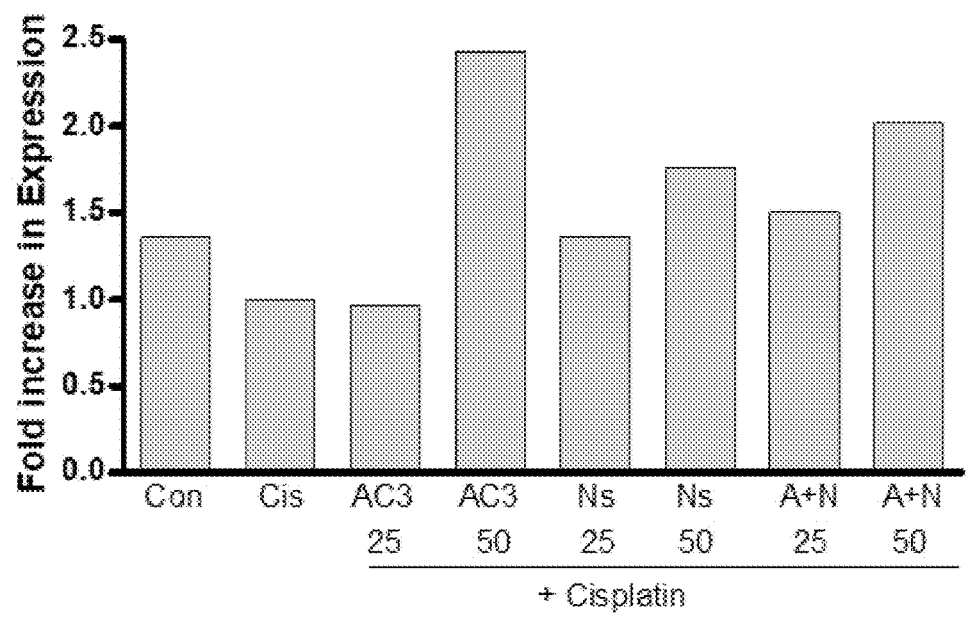
FIG. 20 is a graphical representation showing the increase in the expression of NRF2 levels in kidneys of experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and Nigella sativa extract, individually and in combination.
Figure 21:
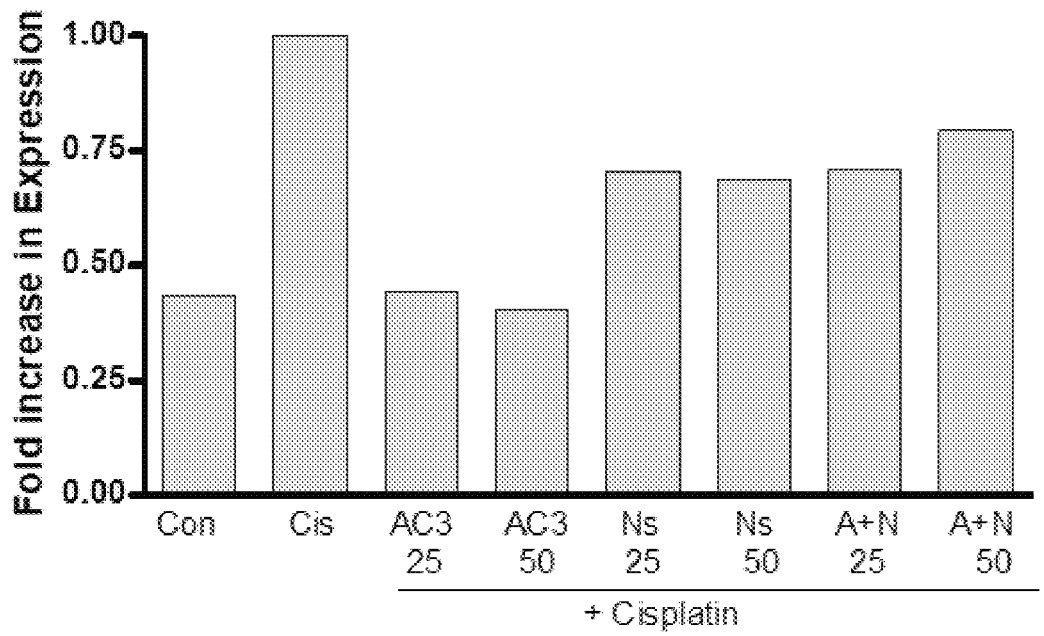
FIG. 21 is a graphical representation showing the decrease in the expression of NFκB in kidneys of experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and *Nigella sativa* extract, individually and in combination.

Nrf2 levels which were decreased by cisplatin administration was normalised by the administration of AC3 complex and NS extract, individually and in combination (FIG. 19 and FIG. 20). Similarly the elevated levels of NF-κB was reduced by the administration of AC3 complex and NS extract, individually and in combination (FIG. 19 and FIG. 21).

Figure 22:
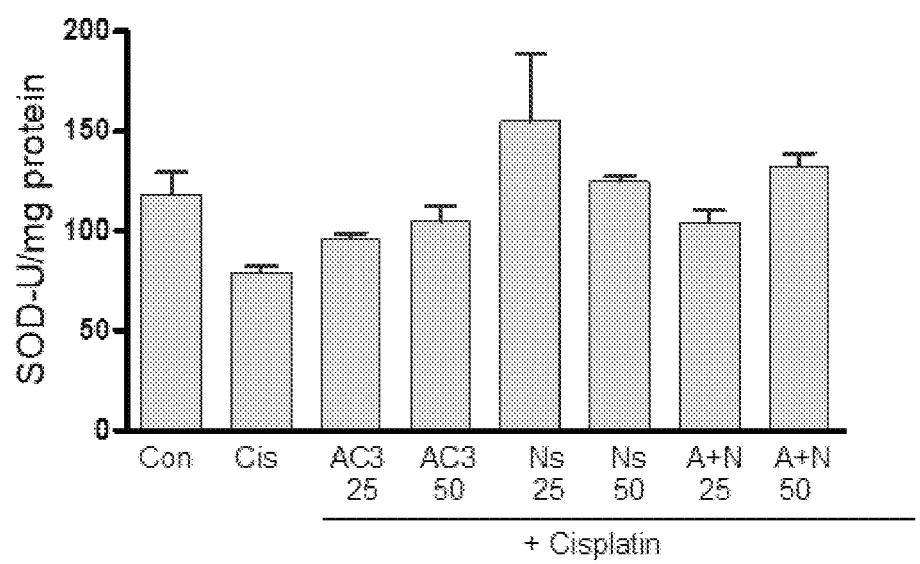
FIG. 22 is a graphical representation showing the increase in the activity of superoxide dismutase in kidneys of experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and *Nigella sativa* extract, individually and in combination.
Figure 23:
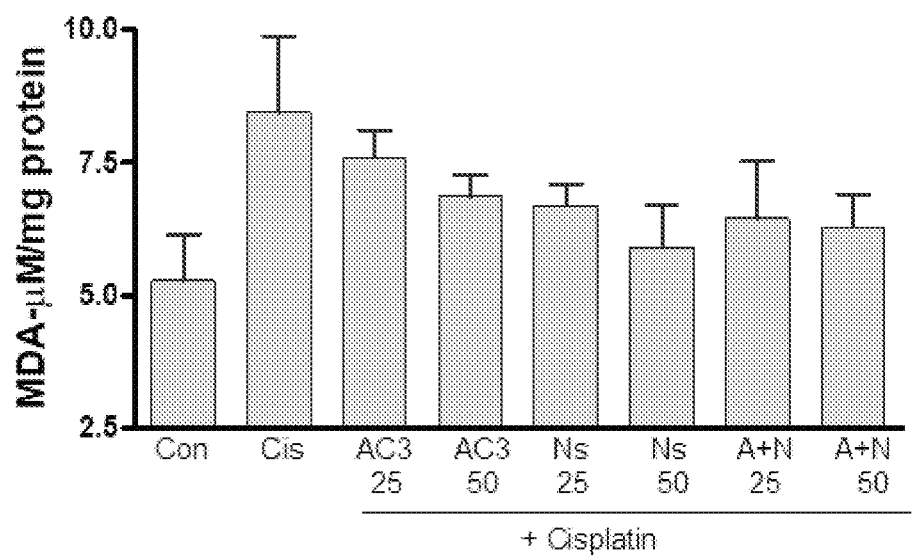
FIG. 23 is a graphical representation showing the decrease in the levels of malondialdehyde in kidneys of experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and *Nigella sativa* extract, individually and in combination.

The superoxide dismutase (SOD) activity was analysed by using a SOD determination kit (Sigma Aldrich 19160) in Kidney lysate. The level of SOD was expressed as U/mg protein. Malondialdehyde, a lipid peroxidation end product in tissue homogenate, was determined according to the method of Beuge and Aust., 1978 with some modifications. The tissue homogenate was mixed with an equal volume of TBA-TCA-HCl solution (0.5% TBA, 20% TCA and 0.25 N HCl). The mixture was heated for 30 min in a boiling water bath (95-100° C.) and cooled immediately. The tubes were centrifuged at 10,000 rpm for 10 min and absorbance of the supernatant was read at 532 nm. The level of lipid peroxides was expressed as µM MDA formed/mg protein. AC3 complex and NS extract, individually and in combination elevated the decreased levels of SOD after cisplatin treatment (FIG. 22) and decreased the MDA levels (FIG. 23).

Among the inflammatory markers, the concentrations of IL-6 and IL-1β in kidney homogenate were carried out by ELISA (R&D Systems (Minneapolis, Minnesota, USA) as per the manufacturer's instructions. The results were expressed as concentration per mg protein for kidney homogenate. TNF-α and IFN-γ were estimated using qRT-PCR as the procedure described before with the following primers:

TABLE 2

List of primers

| Name | Primer sequence (Forward) | Primer sequence (Reverse) |
|---|---|---|
| r TNFα | ACT GAA CTT CGG GGT GAT TG (SEQ ID NO: 9) | GCT TGG TGG TTT GCT ACG AC (SEQ ID NO: 10) |
| r IFN-γ | AGTCTGAAGAACTAT TTTAACTCAAGTAGC AT (SEQ ID NO: 11) | CTGGCTCTCAAGTAT TTTCGTGTTAC (SEQ ID NO: 12) |
| β-actin | CCCGCGAGTACAACC TTCT (SEQ ID NO: 7) | CGTCATCCATGGCGA ACT (SEQ ID NO: 8) |

Figure 24:
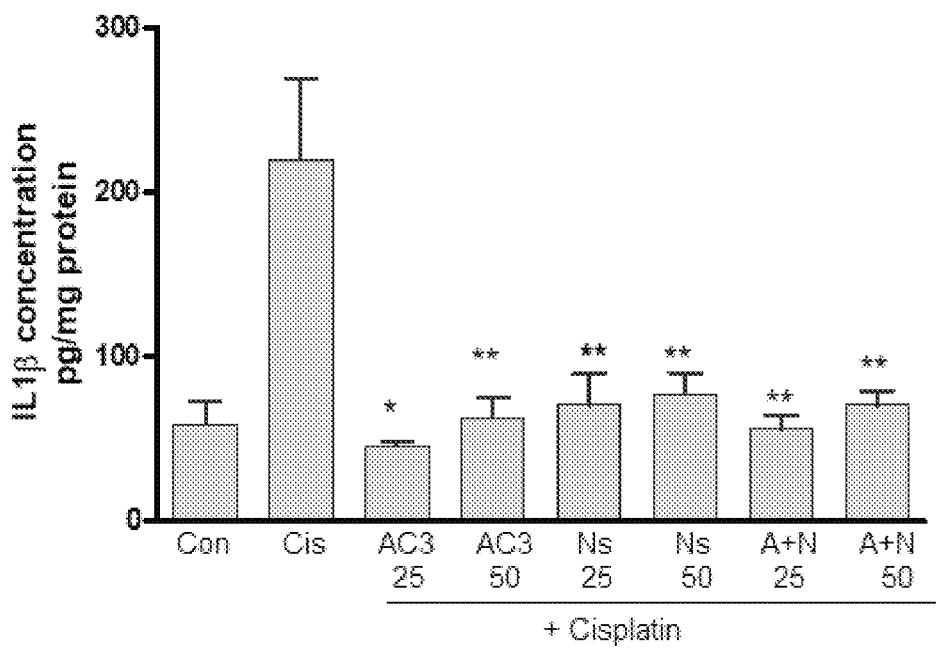
FIG. 24 is a graphical representation showing the decrease in the levels of IL-1β in kidneys of experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and *Nigella sativa* extract, individually and in combination. * $P<0.05$, ** $P<0.01$.
Figure 25:
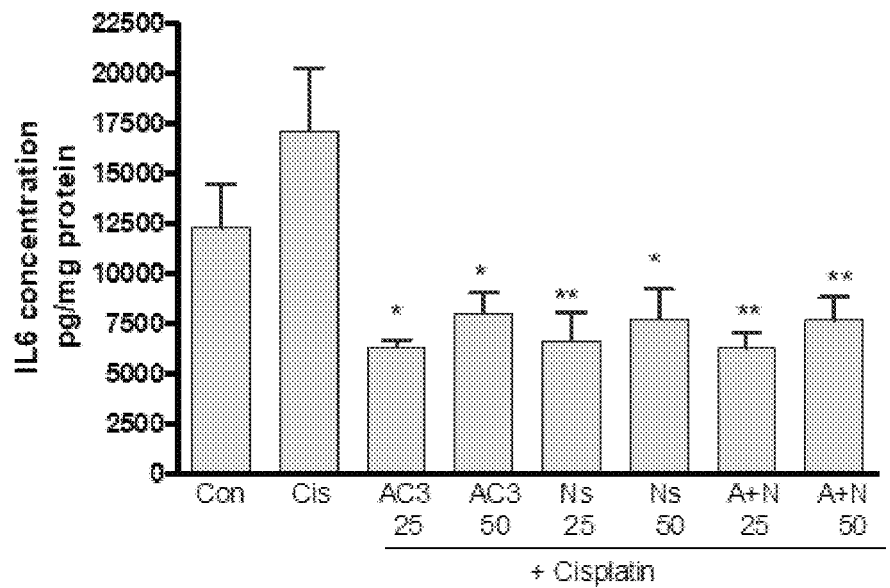
FIG. 25 is a graphical representation showing the decrease in the levels of IL-6 in kidneys of experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and *Nigella sativa* extract, individually and in combination. * $P<0.05$, ** $P<0.01$.
Figure 26:
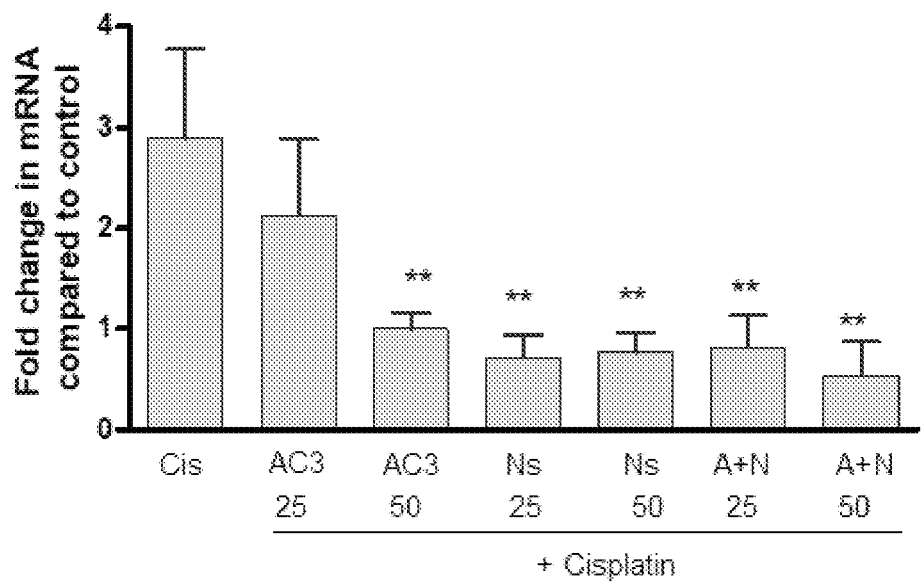
FIG. 26 is a graphical representation showing the decrease in the levels of TNF-α in kidneys of experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and *Nigella sativa* extract, individually and in combination. ** $P<0.01$.
Figure 27:
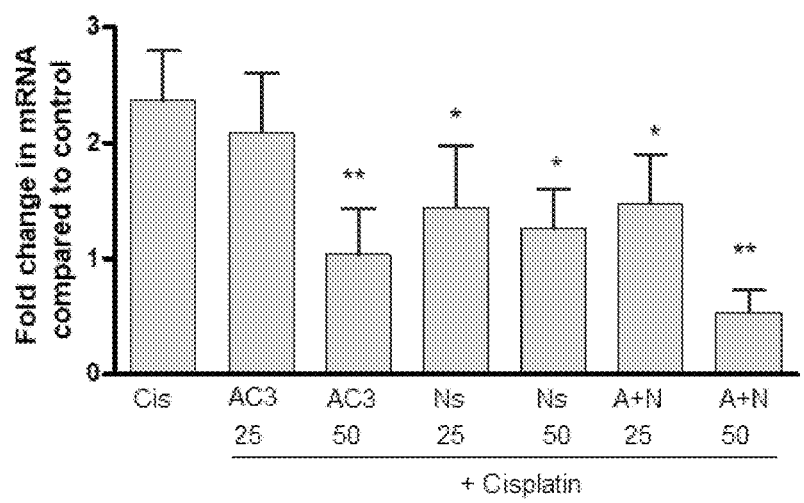
FIG. 27 is a graphical representation showing the decrease in the levels of INF-γ in kidneys of experimental animals by a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and *Nigella sativa* extract, individually and in combination. * $P<0.05$, ** $P<0.01$.

AC3 complex and NS extract, individually and in combination decreased the levels of IL-1β (FIG. 24), IL-6 (FIG. 25), TNF-α (FIG. 26) and IFN-γ (FIG. 27).

Histopathological Analysis

Kidneys were collected and fixed in formaldehyde solution immediately after collection. The tissue samples were dehydrated and embedded in paraffin wax. Serial paraffin sections (4 um) were obtained and kept at 37° C. for more than 12 h. The sections were immersed in three consecutive washings in xylol for 5 min to remove paraffin, and then hydrated with five consecutive washings with alcohol in descending order 100, 95, 80, 70, 50% and deionized water respectively. The histological paraffin sections were then treated with HE staining. Changes in organizational structure were visualized using a light microscope. Histopathological analysis was performed to assess the tubular necrosis, glomerular structure, tubular interstitial fibrosis and necrosis in the kidney of experimental animals.

Figure 28:
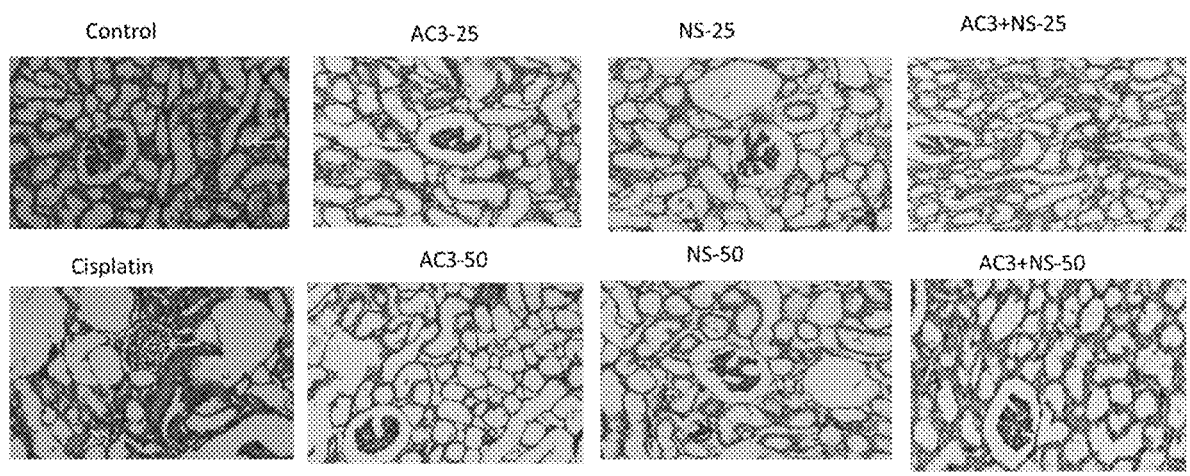
FIG. 28 is a histopathological image of the kidney cross section showing the changes, inflammatory cell invasion (ICI) and necrosis (NS) patterns in glomeruli (G) and bowman's capsule (BC) of experimental animals treated with a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and *Nigella sativa* extract, individually and in combination.
Figure 29:
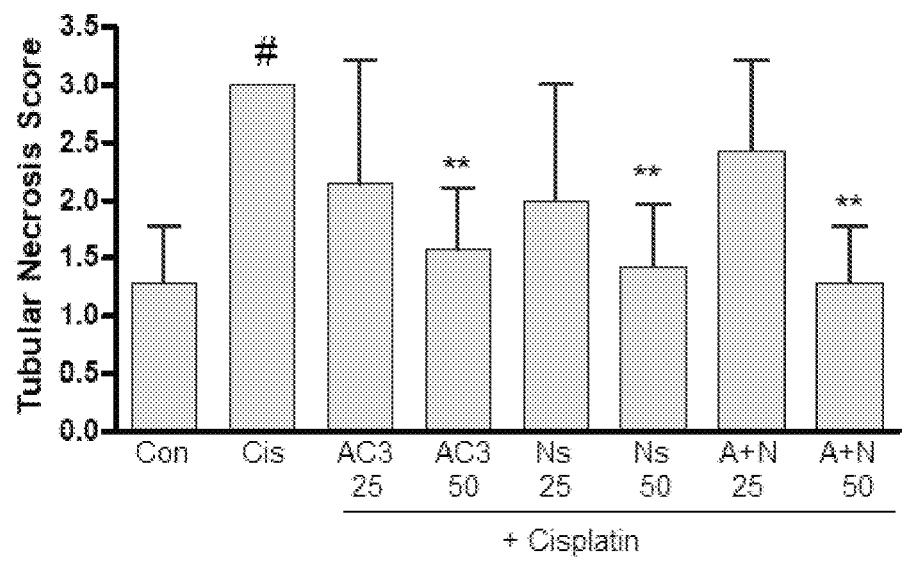
FIG. 29 is a graphical representation showing the decrease in tubular necrosis kidney cross section of experimental animals administered with a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and *Nigella sativa* extract, individually and in combination. ** $P<0.01$.
Figure 30:
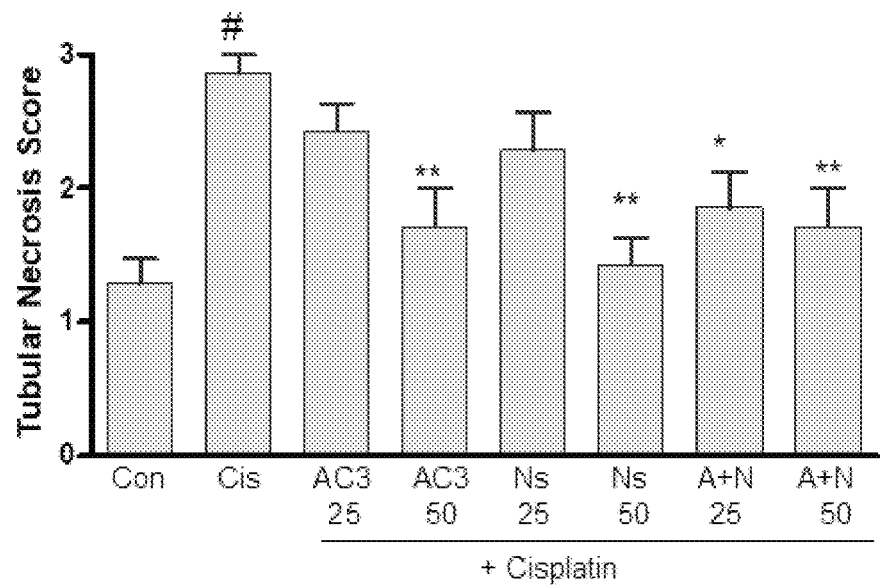
FIG. 30 is a graphical representation showing the changes in glomerular structure of kidney cross section of experimental animals administered with a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and *Nigella sativa* extract, individually and in combination. * $P<0.05$, ** $P<0.01$.
Figure 31:
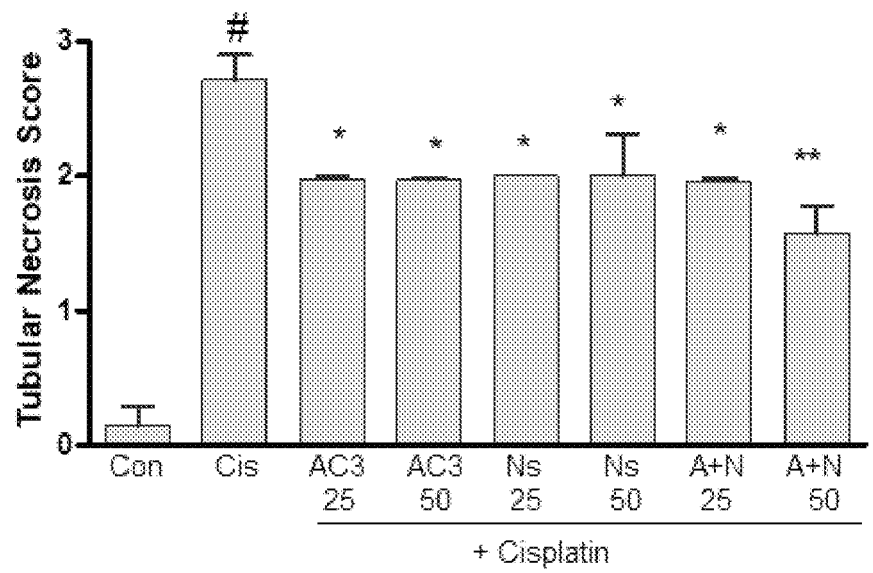
FIG. 31 is a graphical representation showing the decrease in tubular interstitial fibrosis in kidney cross section of experimental animals administered with a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and *Nigella sativa* extract, individually and in combination. * $P<0.05$, ** $P<0.01$.
Figure 32:
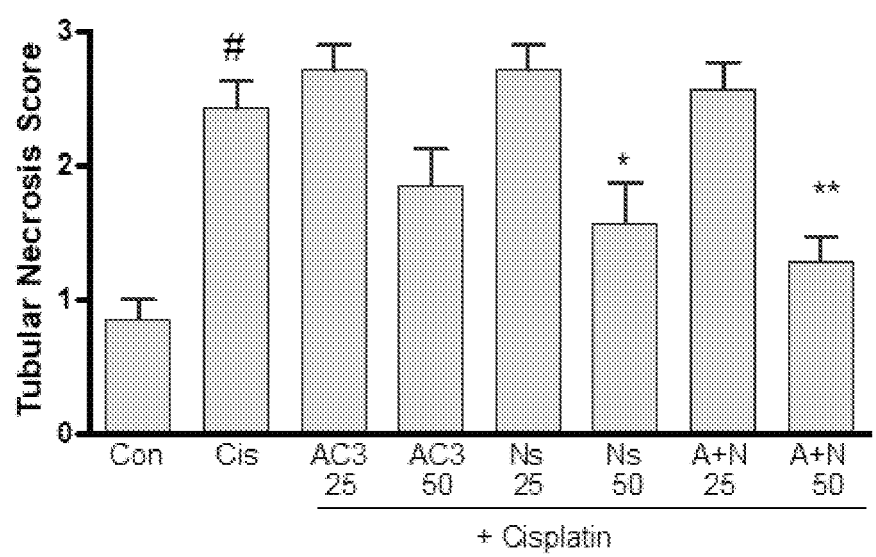
FIG. 32 is a graphical representation showing the decrease in cell necrosis in kidney cross section of experimental animals administered with a composition comprising 20-50% w/w bisdemethoxycurcumin, 10-25% w/w demethoxycurcumin and 30-50% w/w curcumin or 20-50% w/w bisdemethoxycurcumin, 10-25% w/w demethoxycurcumin and 25-50% w/w curcumin, and *Nigella sativa* extract, individually and in combination. * $P<0.05$, ** $P<0.01$.

The results indicated that AC3 complex and NS extract individually and in combination reduced tubular necrosis (FIG. 28 and FIG. 29), improved glomerular structure (FIG. 28 and FIG. 30), reduced tubular interstitial fibrosis (FIG. 28 and FIG. 31) and decreased necrosis (FIG. 28 and FIG. 32) in experimental animals, indicating the nephroprotective effect of both AC3 complex and NS extract.

Overall, the composition comprising 20-80% w/w bisdemethoxycurcumin, 10-35% w/w demethoxycurcumin and 10-50% w/w curcumin individually and in combination with *Nigella sativa* extract standardised to contain not less than 2% w/w thymoquinone, about 0.01%-10% w/w thymohydroquinone, about 15%-95% w/w fatty acids, about 0.001%-3% w/w hederagenin or hederin, provided significant protection against cisplatin induced Kidney injury in vitro and in animal model. The protection was mediated by reduction in oxidative stress and inflammation and reducing the kidney damage by normalizing the damage markers and preventing persistent injury to the kidney. The compositions elucidated their effect by reducing apoptosis and increasing autophagy and can used effectively as a nephroprotective agent.

Example 3: Formulations Containing

The composition is formulated along with pharmaceutically/nutraceutically acceptable excipients, adjuvants, diluents, stabilizing agents, dispersible gums, bioavailability enhancers or carriers and administered orally in the form of tablets, capsules, syrups, gummies, powders, suspensions, emulsions, chewables, candies or eatables.

In a related aspect the bioavailability enhancer is selected from the group of piperine (BioPerine®), quercetin, garlic extract, ginger extract, and naringin. In another related aspect, the stabilizing agent is selected from the group consisting rosmarinic acid, butylated hydroxyanisole, butylated hydroxytoluene, sodium metabisulfite, propyl gallate, cysteine, ascorbic acid and tocopherols. In yet another related aspect, the dispersible gums are selected from the group consisting of Agar, Alginate, Carrageenan, Gum Arabic, Guar Gum, Locust Bean Gum, Konjac Gum, Xanthan Gum and Pectin.

Tables 3-6 provide illustrative examples of nutraceutical formulations containing bisdemethoxycurcumin

TABLE 3

| Tablet |
|---|
| Active Ingredients |
| AC3 complex (Curcumin BD3 Complex)<br>Nigella sativa extract (NIGELLIN ®)<br>Excipients |
| Microcrystalline cellulose, Colloidal silicon dioxide, Magnesium stearate, BioPerine ®, Polyvinylpyrrolidone/starch/Hydroxy propyl methyl cellulose, Hydroxy propyl cellulose |

TABLE 4

| Capsule |
|---|
| Active Ingredients |
| AC3 complex (Curcumin BD3 Complex)<br>Nigella sativa extract (NIGELLIN ®)<br>Excipients |
| Microcrystalline cellulose, BioPerine ® |

TABLE 5

| Powder |
|---|
| Active Ingredients |
| AC3 complex (Curcumin BD3 Complex)<br>Nigella sativa extract (NIGELLIN ®)<br>Excipients |
| BioPerine ®, |

TABLE 6

| Gummy formulation |
|---|
| Active Ingredients |
| AC3 complex (Curcumin BD3 Complex)<br>Excipients |
| BioPerine ®, Gelatin (270 Bloom Mesh 10), Refined Sugar, Glucose Corn Syrup, Citric Acid, Lactic Acid, Water, Natural Mango Flavor M38630, Tartaric Acid, Refined Sugar |

TABLE 7

| Candy formulation |
|---|
| Active Ingredients |
| AC3 complex (Curcumin BD3 Complex)<br>Excipients |
| BioPerine ®, Sucrose, Liquid Glucose, Flavoring agent, Menthol, Acidulants (Citric acid/Tartaric Acid/Maleic Acid), Purified water |

The above formulations are merely illustrative examples, any formulation containing the above active ingredient intended for the said purpose will be considered equivalent.

Other modifications and variations of the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention and is to be interpreted only in conjunction with the appended claims.

We claim:

1. A method for therapeutic management of toxicity in mammalian kidney cells comprising bringing into contact mammalian kidney cells with a composition consisting essentially of 20-80% w/w bisdemethoxycurcumin, 10-35% w/w demethoxycurcumin, 10-50% w/w curcumin, and a *Nigella sativa* extract, to reduce toxic effects in cells.

2. The method as in claim 1, wherein the composition consists essentially of 30-50% w/w of the bisdemethoxycurcumin, 10-25% w/w of the demethoxycurcumin, 30-50% of the w/w curcumin and the *Nigella sativa* extract.

3. The method as in claim 1, wherein the composition consists essentially of 30-50% w/w of the bisdemethoxycurcumin, 10-25% w/w of the demethoxycurcumin, 25-45% of the w/w curcumin and the *Nigella sativa* extract.

4. The method as in claim 1, wherein the composition consists essentially of 20-50% w/w of the bisdemethoxycurcumin, 10-25% w/w of the demethoxycurcumin, 25-45% of the w/w curcumin and the *Nigella sativa* extract.

5. The method as in claim 1, wherein the composition consists essentially of 20-50% w/w of the bisdemethoxycurcumin, 10-25% w/w of the demethoxycurcumin, 30-50% of the w/w curcumin and the *Nigella sativa* extract.

6. The method as in claim 1, wherein a total curcuminoids concentration in the composition is 20-95% w/w.

7. The method as in claim 1, wherein the *Nigella sativa* extract is standardised to contain not less than 2% w/w thymoquinone, from about 0.01% to 10% w/w thymohydroquinone, from about 15% to 95% w/w fatty acids, and from about 0.001% to 3% w/w hederagenin or hederin.

8. The method as in claim 1, wherein reduction in toxic effects in the cells is brought about by preventing apoptosis and promoting autophagy.

9. The method as in claim 1, wherein the mammalian kidney cells are human cells.

10. A method for therapeutic management of nephrotoxicity in mammals comprising administering an effective dose of a composition consisting essentially of 20-80% w/w bisdemethoxycurcumin, 10-35% w/w demethoxycurcumin, 10-50% w/w curcumin, and a *Nigella sativa* extract, to mammals with symptoms of nephrotoxicity to bring about nephroprotection.

11. The method as in claim 10, wherein the composition consists essentially of 30-50% w/w of the bisdemethoxycurcumin, 10-25% w/w of the demethoxycurcumin, 30-50% of the w/w curcumin and the *Nigella sativa* extract.

12. The method as in claim 10, wherein the composition consists essentially of 30-50% w/w of the bisdemethoxycurcumin, 10-25% w/w of the demethoxycurcumin, 25-45% of the w/w curcumin and the *Nigella sativa* extract.

13. The method as in claim 10, wherein the composition consists essentially of 20-50% w/w of the bisdemethoxycurcumin, 10-25% w/w of the demethoxycurcumin, 25-45% of the w/w curcumin and the *Nigella sativa* extract.

14. The method as in claim 10, wherein the composition consists essentially of 20-50% w/w of the bisdemethoxycurcumin, 10-25% w/w of the demethoxycurcumin, 30-50% of the w/w curcumin and the *Nigella sativa* extract.

15. The method as in claim 10, wherein a total curcuminoids concentration in the composition is 20-95% w/w.

16. The method as in claim 10, wherein the symptoms of nephrotoxicity comprise elevated urine albumin levels, decrease urine uric acid levels, elevated blood urea nitrogen levels, elevated serum creatinine levels, anorexia, fatigue, mental status changes, nausea, vomiting, or pruritus.

17. The method as in claim 10, wherein the *Nigella sativa* extract standardised to contain not less than 2% w/w thymoquinone, from about 0.01% to 10% w/w thymohydroquinone, from about 15% to 95% w/w fatty acids, and from about 0.001% to 3% w/w hederagenin or hederin.

18. The method as in claim 10, wherein nephroprotection is brought about by preventing apoptosis and promoting autophagy.

19. The method as in claim 10, wherein nephrotoxicity is induced by agents selected from the group consisting of drugs, ethylene glycol, carbon tetrachloride, sodium oxalate, heavy metals selected from lead, mercury, cadmium and arsenic, biological agents selected from viruses, mould and fungi, interferons, recombinant leukocytes and antibiotics.

20. The method as in claim 10, wherein the effective dose is 25 to 50 mg/kg bodyweight of the said mammal.

21. The method as in claim 10, wherein the therapeutic management is brought about by decreasing elevated levels of serum and urine uric acid, urine albumin and blood urea nitrogen.

22. The method as in claim 10, wherein the therapeutic management is brought about by decreasing oxidative stress and inflammation.

23. The method as in claim 10, wherein the therapeutic management is brought about by preventing apoptosis and promoting autophagy.

24. The method as in claim 10, wherein the therapeutic management is brought about by decreasing elevated levels of kidney injury markers selected from the group consisting of kidney injury molecule 1 (KIM 1), N-acetyl-$\beta$-D-glucosaminidase (NAG), and Neutrophil gelatinase-associated lipocalin (NGAL).

25. The method as in claim 10, wherein therapeutic management is brought about by decreasing tubular necrosis, tubular interstitial fibrosis, cell necrosis and improving glomerular structure in kidneys of the mammal.

26. The method as in claim 10, wherein the composition is administered orally as tablets, capsules, syrups, gummies, powders, suspensions, emulsions, chewables, candies or eatables.

27. The method as in claim 10, wherein the mammal is human.

* * * * *